US007132587B2

(12) United States Patent
Kikuchi et al.

(10) Patent No.: US 7,132,587 B2
(45) Date of Patent: Nov. 7, 2006

(54) NON-AUTONOMOUS TRANSPOSON GENE OF RICE, TRANSFORMED PLANT AND METHOD OF USE

(75) Inventors: Kazuhiro Kikuchi, Okazaki (JP); Hiroyuki Hirano, Tokyo (JP); Masamitsu Wada, Tokyo (JP)

(73) Assignee: Agency of Industrial Science and Technology, Saitama (JP)

( * ) Notice: Subject to any disclaimer, the term of this patent is extended or adjusted under 35 U.S.C. 154(b) by 0 days.

(21) Appl. No.: 10/494,944

(22) PCT Filed: Nov. 6, 2002

(86) PCT No.: PCT/JP02/11585

§ 371 (c)(1),
(2), (4) Date: Sep. 29, 2004

(87) PCT Pub. No.: WO03/040363

PCT Pub. Date: May 15, 2003

(65) Prior Publication Data
US 2005/0125854 A1     Jun. 9, 2005

(30) Foreign Application Priority Data

| Nov. 8, 2001 | (JP) | ............................. | 2001-343002 |
| Jan. 18, 2002 | (JP) | ............................. | 2002-009729 |
| Jun. 7, 2002 | (JP) | ............................. | 2002-167345 |
| Aug. 12, 2002 | (JP) | ............................. | 2002-234412 |

(51) Int. Cl.
*C12N 15/01* (2006.01)
*C12Q 12/68* (2006.01)

(52) U.S. Cl. ...................................... 800/276; 435/91.2

(58) Field of Classification Search ............... 536/23.1, 536/23.6; 435/468, 410, 320.1; 800/278, 800/291, 295, 298
See application file for complete search history.

(56) References Cited

U.S. PATENT DOCUMENTS 5,965,791 A    10/1999  Ebinuma ................. 800/278

FOREIGN PATENT DOCUMENTS

| EP | 716147 A1 | 6/1996 |
| EP | 1275719 A1 | 1/2003 |
| JP | 9-154580 A | 6/1997 |
| JP | 2001-343002 | 11/2001 |
| JP | 2002-009729 | 1/2002 |
| JP | 2002-167345 | 6/2002 |
| JP | 2002-234412 | 8/2002 |
| WO | WO 96/15252 A1 | 5/1996 |
| WO | WO 01/32881 | * 10/2001 |
| WO | WO 01/73036 A1 | 10/2001 |

OTHER PUBLICATIONS

Yano et al. Hd1, a Major Photoperiod Sensitivity Quantitative Trait Locus in Rice, Is Closely Related to the *Arabidopsis* Flowering Time Gene CONSTANS (2000) Plant Cell vol. 12 pp. 2473-2483.*
Kikuchi et al. The Plant MITE mPING is Mobilized in Anther Culture (2003) Nature vol. 421, pp. 167-170.*
Jurka, J. et al. "PIFs meet Tourists and Harbingers: A superfamily Reunion", *PNAS*, vol. 98(22) pp. 12315-12316, 2001.
Zhang, X. et al. "P instability factor: An active maize transposon system associated with the amplification of Tourist-like MITEs and a new superfamily of transposases", *PNAS Early Edition*, pp. 1-6, 2001.
Scortecci, K. C. et al. "Somatic Excision of the Ac Transposable Element in Transgenic *Arabidopsis thaliana* after 5-Azacytidine Treatment", Plant Cell Physiol., vol. 38(3) pp. 336-343, 1997.
Sano, H. et al. "A single treatment of rice seedlings with 5-azacytidine induces heritable dwarfism and undermethylation of genomic DNA", Mol Gen Genet, vol. 220 pp. 441-447, 1990.
Le, Q.H. et al. "Tc8, a Tourist-like Transposon in *Caenorhabditis elegans*", Genetics, vol. 158 pp. 1081-1088, 2001.
Nakazaki, T. et al. "Polymorphic insertion of transposon-like sequence in mutable slender-granule gene slg locus", Japanese Society of Breeding 100th Conference, Autumn meeting, Oct. 2001; This is the English translation of this paper, first cited in IDS filed Sep. 29, 2004 for this application.
Database EMBL 'Online! May 24, 2001, "Oryza sativa (japonica cultivar-group) genomic DNA, chromosome 1, BAC clone: B1158C05." XP 002359806 (abstract).
Database EMBL 'Online! Aug. 2, 2001, "Oryza sativa (japonica cultivar-group) genomic DNA, chromosome 6, BAC clone: OJ1057_A09, Working Draft Sequence, 1 ordered pieces." XP002359807 (abstract).
Database EMBL 'Online! May 31, 2001, "Oryza sativa (japonica cultivar-group) genomic DNA, chromosome 6, PAC clone: PO656E03." XP002359808 (abstract).
Turcotte Kime et al., "Survey of transposable elements from rice genomic sequences," Plant Journal, vol. 25, No. 2, Jan. 2001, pp. 169-179, XP002359802, Publisher: Blackwell Sciences, Oxford, England.
Chang-Gyun Han et al., "New transposable elements identified as insertions in rice transposon Tnr1," Genes Genet. Syst., 2000, vol. 75, pp. 69-77.
Thomas E. Bureau et al., "A computer-based systematic survey reveals the predo, onance of small inverted-repeat elements in wild-type rice genes," Proc. Natl. Acad. Sci. USA, 1996, vol. 93, pp. 8524-8529; Publisher: National Academy of Sciences, Washington, D.C.
Long Mao et al., "Rice Transposable Elements: A Survey of 73,000 Sequence-Tagged-Connectors," Genome Research, 2000, vol. 10, pp. 982-990.

* cited by examiner

*Primary Examiner*—Ashwin D. Mehta
*Assistant Examiner*—Cathy Kingdon Worley
(74) *Attorney, Agent, or Firm*—Drinker Biddle & Reath LLP

(57) ABSTRACT

The invention includes a method of transposing a non-autonomous transposon gene of rice (*Oryza sativa*). The method comprises culturing anthers of rice or treating roots, seeds, leaves, and stems of axillary buds of rice, or a callus derived from them, with 5-azacytidine or 5-azadeoxycytidine. Also included in the invention is a plant or plant seeds produced by the method.

3 Claims, 11 Drawing Sheets

Figure 1

| | | | | | |
|---|---|---|---|---|---|
| 144010 | 144020 | 144030 | 144040 | 144050 | 144060 |
| TTTCAAGTAC | AATCTCAACT | TAGGGAAAGT | TGTGATTGAG | GGAGGATGTT | AGATAATGTT |
| 144070 | 144080 | 144090 | 144100 | 144110 | 144120 |
| AGTTAGTTTG | TTATAGAGAT | AGATTAGTTC | TGTTACCGCA | TGTACTTTCT | TGTATCTATC |
| 144130 | 144140 | 144150 | 144160 | 144170 | 144180 |
| TCTATATCCA | GGATTGTCTC | AGGTTGTTGA | GATTAATCCT | ATCCTTTGTA | CACGCCACGG |
| 144190 | 144200 | 144210 | 144220 | 144230 | 144240 |
| TAGAGGCTCT | TTCTGCCTAT | ATCAACAAAG | GTGCGGCCCC | GTAAAGGGGT | TCAACGCTTC |
| 144250 | 144260 | 144270 | 144280 | 144290 | 144300 |
| TCATTCCGTT | TTACAATCCT | CCTTCTTCCT | CCTGGTGTTG | GAAATTCGTT | GATCGAGTTG |
| 144310 | 144320 | 144330 | 144340 | 144350 | 144360 |
| AAACTCTCAT | CCTTCATCAT | GTGCTGCAGA | AACTAACGCG | TGCACAGATG | ATGGATGGGT |
| 144370 | 144380 | 144390 | 144400 | 144410 | 144420 |
| GTGGTGTGAC | ATGAAAGTGG | ATCAATGACA | CGCGGCACAT | TTAGGGGAGT | GTGTCGTGTC |
| 144430 | 144440 | 144450 | 144460 | 144470 | 144480 |
| TTGACTTCTT | CATGCAAAAG | TATACCAACC | CTGTATAAGG | CCAGTCACAA | TGGCTAGTGT |
| 144490 | 144500 | 144510 | 144520 | 144530 | 144540 |
| CATTGCACGG | CTACCCAAAA | TATTATACCA | TCTTCTCTCA | AATGAAATCT | TTTATGAAAC |
| 144550 | 144560 | 144570 | 144580 | 144590 | 144600 |
| AATCCCCACA | GTGGAGGGGT | TTCACTTTGA | CGTTTCCAAG | ACTAAGCAAA | GCATTTAATT |
| 144610 | 144620 | 144630 | 144640 | 144650 | 144660 |
| GATACAAGTT | GCTGGGATCA | TTTGTACCCA | AAATCCGGCG | CGGCGCGGGA | GAATGCGGAG |
| 144670 | 144680 | 144690 | 144700 | 144710 | 144720 |
| GTCGCACGGC | GGAGGCGGAC | GCAAGAGATC | CGGTGAATGA | AACGAATCGG | CCTCAACGGG |
| 144730 | 144740 | 144750 | 144760 | 144770 | 144780 |
| GGTTTCACTC | TGTTACCGAG | GACTTGGAAA | CGACGCTGAC | GAGTTTCACC | AGGATGAAAC |
| 144790 | 144800 | 144810 | 144820 | 144830 | 144840 |
| TCTTTCCTTC | TCTCTCATCC | CCATTTCATG | CAAATAATCA | TTTTTTATTC | AGTCTTACCC |
| 144850 | 144860 | 144870 | 144880 | 144890 | 144900 |
| CTATTAAATG | TGCATGACAC | ACCAGTGAAA | CCCCCATTGT | GACTGGCCTA | AGCATCTTTG |

3' LTR

Inverted Repeats

Figure 2

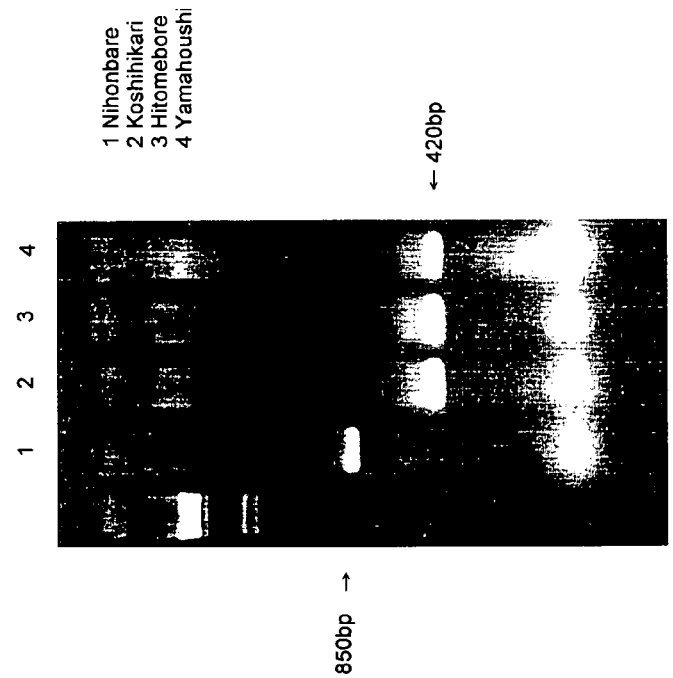

```
L05           ATGTAGTTTG TCGGTAAGTT TGATTATCAC GGTAACCACA AGTCAAGGGA
  AzaC-callus1 ATGTAGTTTG TCGGTAAGTT TGATTATCAC GGTAACCACA AGTCAAGGGA
  AzaC-callus2 ATGTAGTTTG TCGGTAAGTT TGATTATCAC GGTAACCACA AGTCAAGGGA
  AzaC-callus3 ATGTAGTTTG TCGGTAAGTT TGATTATCAC GGTAACCACA ----------
  AzaC-callus4 ATGTAGTTTG TCGGTAAGTT TGATTATCaC GGTAAC---- ----------

L05           AAGATATGGA CTCCTTAATA AGGCCAGTCA CAATGGGGGT TTCACTGGTG
  AzaC-callus1 AAGATATGGA CTCCTTAA-- ---------- ---------- ----------
  AzaC-callus2 AAGATATGGA CTCCTTAATA A--------- ---------- ----------
  AzaC-callus3 ---------- ---------- ---------- ---------- ----------
  AzaC-callus4 ---------- ---------- ---------- ---------- ----------

L05           TGTCATGCAC ATTTAATAGG GGTAAGACTG AATAAAAAAT GATTATTTGC
  AzaC-callus1 ---------- ---------- ---------- ---------- ----------
  AzaC-callus2 ---------- ---------- ---------- ---------- ----------
  AzaC-callus3 ---------- ---------- ---------- ---------- ----------
  AzaC-callus4 ---------- ---------- ---------- ---------- ----------

L05           ATGAAATGGG GATGAGAGAG AAGGAAAGAG TTTCATCCTG GTGAAACTCG
  AzaC-callus1 ---------- ---------- ---------- ---------- ----------
  AzaC-callus2 ---------- ---------- ---------- ---------- ----------
  AzaC-callus3 ---------- ---------- ---------- ---------- ----------
  AzaC-callus4 ---------- ---------- ---------- ---------- ----------

L05           TCAGCGTCGT TTCCAAGTCC TCGGTAACAG AGTGAAACCC CCGTTGAGGC
  AzaC-callus1 ---------- ---------- ---------- ---------- ----------
  AzaC-callus2 ---------- ---------- ---------- ---------- ----------
  AzaC-callus3 ---------- ---------- ---------- ---------- ----------
  AzaC-callus4 ---------- ---------- ---------- ---------- ----------

L05           CGATTCGTTT CATTCACCGG ATCTCTTGCG TCCGCCTCCG CCGTGCGACC
  AzaC-callus1 ---------- ---------- ---------- ---------- ----------
  AzaC-callus2 ---------- ---------- ---------- ---------- ----------
  AzaC-callus3 ---------- ---------- ---------- ---------- ----------
  AzaC-callus4 ---------- ---------- ---------- ---------- ----------

L05           TCCGCATTCT CCCGCGCCGC GCCGGATTTT GGGTACAAAT GATCCCAGCA
  AzaC-callus1 ---------- ---------- ---------- ---------- ----------
  AzaC-callus2 ---------- ---------- ---------- ---------- ----------
  AzaC-callus3 ---------- ---------- ---------- ---------- ----------
  AzaC-callus4 ---------- ---------- ---------- ---------- ----------

L05           ACTTGTATCA ATTAAATGCT TGCTTAGTC TTGGAAACGT CAAAGTGAAA
  AzaC-callus1 ---------- ---------- ---------- ---------- ----------
  AzaC-callus2 ---------- ---------- ---------- ---------- ----------
  AzaC-callus3 ---------- ---------- ---------- ---------- ----------
  AzaC-callus4 ---------- ---------- ---------- ---------- ----------

L05           CCCCTCCACT GTGGGGATTG TTTCATAAAA GATTTCATTT GAGAGAAGAT
  AzaC-callus1 ---------- ---------- ---------- ---------- ----------
  AzaC-callus2 ---------- ---------- ---------- ---------- ----------
  AzaC-callus3 ---------- ---------- ---------- ---------- ----------
  AzaC-callus4 ---------- ---------- ---------- ---------- ----------

L05           GGTATAATAT TTTGGGTAGC CGTGCAATGA CACTAGCCAT TGTGACTGGC
  AzaC-callus1 ---------- ---------- ---------- ---------- ----------
  AzaC-callus2 ---------- ---------- ---------- ---------- ----------
  AzaC-callus3 ---------- ---------- ---------- ---------- ----------
  AzaC-callus4 ---------- ---------- ---------- ---------- ----------

L05           CTAACACTGA ACTGATCAAA GAGCATTTAT TATGGAAAGA TGATTGTGTC
  AzaC-callus1 ----CACTGA ACTGATCAAA GAGCATTTAT TATGGAAAGA TGATTGTGTC
  AzaC-callus2 ----CACTGA ACTGATCAAA GAGCATTTAT TATGGAAAGA TGATTGTGTC
  AzaC-callus3 ------CTGA ACTGATCAAA GAGCATTTAT TATGGAAAGA TGATTGTGTC
  AzaC-callus4 -----ACTGA ACTGATCAAA GAGCATTTAT TATGGAAAGA TGATTGTGTC
```

Figure 9
Sequence number 2
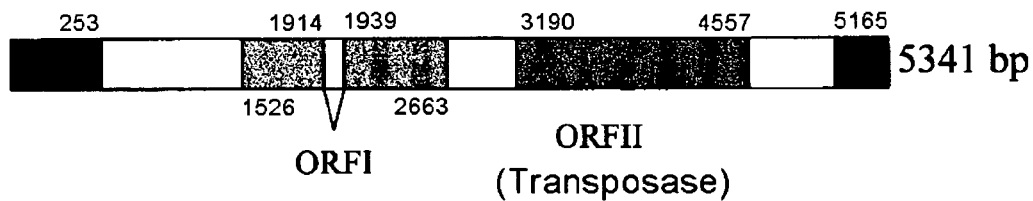
Sequence number 3
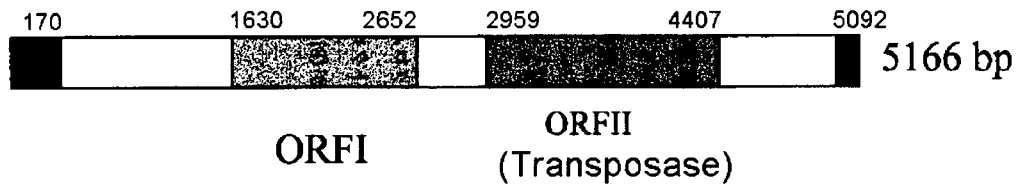
Figure 10
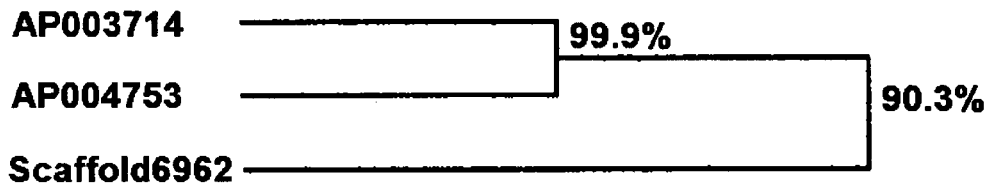
Figure 11
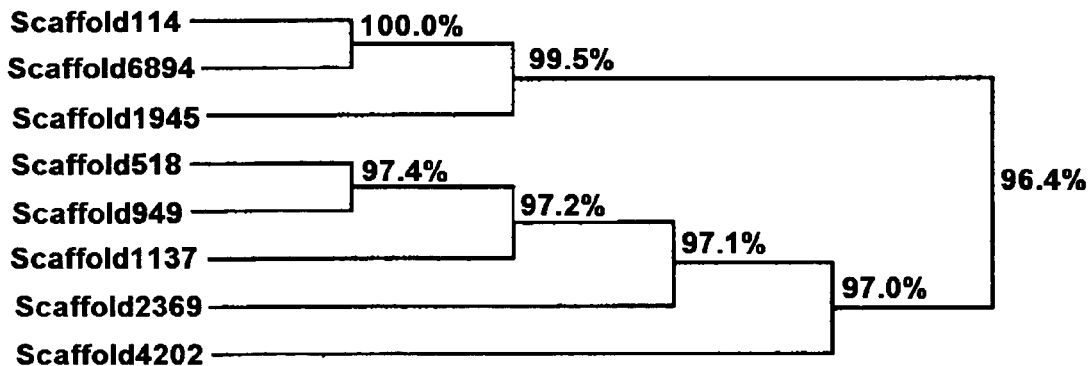

Figure 12

```
                                                            MS GNENQIPVSL
MQSLAISLLL  SETHSLFSHT  KTSSLLSLLF  LSSSKMSEQN  TDGSQVPVNL
                                                 *  ** *
LDEFLAEDEI  MDEIMDDVLH  EMMVLLQSSI  GDLEREAADH  RLHPRKHIKR
LDEFLAEDEI  ID----DLLT  EATVVVQSTI  EGLQNEASDH  RHHPRKHIKR
**********  *    *  *   *  *  ** *   *  ** **  *  *******
PREEAHQNLV  NDYFSENPLY  PSNIFRRRFR  MYRPLFLRIV  DALGQWSDYF
PREEAHQQLV  NDYFSENPLY  PSKIFRRRFR  MSRPLFLRIV  EALGQWSVYF
*******  **  **********  **  *******  *  ********  ******  **
TQRVDAAGRQ  GLSPLQKCTA  AIRQLATGSG  ADELDEYLKI  GETTAMDAMK
TQRVDAVNRK  GLSPLQKCTA  AIRQLATGSG  ADELDEYLKI  GETTAMEAMK
******   *  **********  **********  **********  ******  ***
NFVKGIREVF  GERYLRRPTV  EDTERLLELG  ERRGFPGMFG  SIDCMHWQWE
NFVKGLQDVF  GERYLRRPTM  EDTERLLQLG  EKRGFPGMFG  SIDCMHWHWE
*****    **  *********   *******  **  * ********  *******  **
RCPTAWKGQF  TRGDQKVPTL  ILEAVASHDL  WIWHAFFGVA  GSNNDINVLS
RCPVAWKGQF  TRGDQKVPTL  ILEAVASHDL  WIWHAFFGAA  GSNNDINVLN
***  ******  **********  **********  ********  *  *********
RSTVFINELK  GQAPRVQYMV  NGNQYNEGYF  LADGIYPEWK  VFAKSYRLPI
QSTVFIKELK  GQAPRVQYMV  NGNQYNTGYF  LADGIYPEWA  VFVKSIRLPN
*****  ***  **********  ******  ***  **********  **  **  ***
                                    DXG/AF/F motif
TEKEKLYAQH  QEGARKDIER  AFGVLQRRFC  ILKRPARLYD  RGVLRDVVLG
TEKEKLYADM  QEGARKDIER  AFGVLQRRFC  ILKRPARLYD  RGVLRDVVLA
********    **********  **********  **********  *********
            YREK motif
CIILHNMIVE  DEKEARLIEE  NLDLNEPASS  STVQAPEFSP  DQHVPLERIL
CIILHNMIVE  DEKETRIIEE  DLDLNVPPSS  STVQEPEFSP  EQNTPFDRVL
**********  ****  *  ***  ****  *  **  ****  *****   *   *  *
EKDTSMRDRL  AHRRLKNDLV  EHIWNKFGGG  AHSSGNYVFI  LHY
EKDISIRDRA  AHNRLKKDLV  EHIWNKFGGA  AHRTGN
***  *  ***  **  ***  ***  *********  **   **
```

1. Nihonbare
2. Koshihikari
3. Taichung No 65
4. Kasarasu

1. Taichung No 65
2. Nihonbare
3-6. Gene-transduced Anther-derived callus

Figure 17

L02 GCGTGGACAC ACTGATTGGC CTGACAAAAC ATAGTTAGCA ATTTGCATTA
Seq GCGTGGACAC ACTGATTGGC CTGACAAAAC ATAGTTAGCA ATT------

L02 GGCCAGTCAC AATGGCTAGT GTCATTGCAC GGCTACCCAA AATATTATAC
Seq ----------------------------------------------

L02 CATCTTCTCT CAAATGAAAT CTTTTATGAA ACAATCCCCA CAGTGGAGGG
Seq ----------------------------------------------

L02 GTTTCACTTT GACGTTTCCA AGACTAAGCA AAGCATTTAA TTGATACAAG
Seq ----------------------------------------------

L02 TTGCTGGGAT CATTTGTACC CAAAATCCGG CGCGGCGCGG GAGAATGCGG
Seq ----------------------------------------------

L02 AGGTCGCACG GCGGAGGCGG ACGCAAGAGA TCCGGTGAAT GAAACGAATC
Seq ----------------------------------------------

L02 GGCCTCAACG GGGGTTTCAC TCTGTTACCG AGGACTTGGA AACGACGCTG
Seq ----------------------------------------------

L02 ACGAGTTTCA CCAGGATGAA ACTCTTTCCT TCTCTCTCAT CCCCATTTCA
Seq ----------------------------------------------

L02 TGCAAATAAT CATTTTTTAT TCAGTCTTAC CCCTATTAAA TGTGCATGAC
Seq ----------------------------------------------

L02 ACACCAGTGA AACCCCCATT GTGACTGGCC TTACGGCAAC ATTTGGATAT
Seq ----------------------------------------------

L02 CGAATTATGT CCAAAGAGCG AAGGTATCTG TTAGCTAATC ATCGATCGG
Seq ------ATGT CCAAAGAGCG AAGGTATCTG TTAGCTAATC ATCGATCGG

Figure 18

L06 TGGTCCTCGA TACTGTTGCC TGTTGGTACG GCACCACACC ACTCTGTTTT
Seq TGGTCCTCGA TACTGTTGCC TGTTGGTACG GCACCACACC ACTCTGTTTT

L06 TATTAGGCCA GTCACAATGG CTAGTGTCAT TGCACGGCTA CCCAAAATAT
Seq TATTAG————— —————————— —————————— —————————— ——————————

L06 TATACCATCT TCTCTCAAAT GAAATCTTTT ATGAAACAAT CCCCACAGTG
Seq ————————— —————————— —————————— —————————— ——————————

L06 GAGGGGTTTC ACTTTGACGT TTCCAAGACT AAGCAAAGCA TTTAATTGAT
Seq ————————— —————————— —————————— —————————— ——————————

L06 ACAAGTTGCT GGGATCATTT GTACCCAAAA TCCGGCGCGG CGCGGGAGAA
Seq ————————— —————————— —————————— —————————— ——————————

L06 TGCGGAGGTC GCACGGCGGA GGCGGACGCA AGAGATCCGG TGAATGAAAC
Seq ————————— —————————— —————————— —————————— ——————————

L06 GAATCGGCCT CAACGGGGGT TCACTCTGT TACCGAGGAC TTGGAAACGA
Seq ————————— —————————— —————————— —————————— ——————————

L06 CGCTGACGAG TTTCACCAGG ATGAAACTCT TTCCTTCTCT CTCATCCCCA
Seq ————————— —————————— —————————— —————————— ——————————

L06 TTTCATGCAA ATAATCATTT TTTATTCAGT CTTACCCCTA TTAAATGTGC
Seq ————————— —————————— —————————— —————————— ——————————

L06 ATGACACACC AGTGAAACCC CCATTGTGAC TGGCCTTAGA GGTAAGTTTG
Seq ————————— —————————— —————————— ————————A  GGTAAGTTTG

L06 ATAGTACAGC CCACTACCAG CTCTAAATCA GTCAATGTAG TAGCTAATTC
Seq ATAGTACAGC CCACTACCAG CTCTAAATCA GTCAATGTAG TAGCTAATTC

NON-AUTONOMOUS TRANSPOSON GENE OF RICE, TRANSFORMED PLANT AND METHOD OF USE

RELATED APPLICATIONS

This application claims priority to PCT JP02/11585, and to Japanese Patent Application Nos. 2001-343002, 2002-9729, 2002-167345.

FIELD OF THE INVENTION

The present invention relates to a nonautonomous transposon gene, autonomous transposon gene and transposase gene of rice (Oryza sativa); and a method to transpose the transposon gene; and transformed plants by the transposition.

DESCRIPTION OF THE BACKGROUND

A gene disruption method has been used as a tool to analyze genome of rice (Oryza sativa). To disrupt genomes of rice, a method to activate a segregation factor by mating an individual, wherein a transposase gene (transposition enzyme) is tranduced as an activator, with an individual, wherein a segregation factor is introduced; a method to use T-DNA; and a method to use retrotransposon have been known. However, analysis of spontaneous mutants of rice has not served to find active transposons (Supplementary volume of Cell Engineering, Plant cell engineering series 14, "Plant genome research protocols" 2000, February, Shujun press Co.).

On the other hand, a genome sequencing project is determining the nucleotide sequences of many plants as well as rice and the results are databanked. Furthermore, transposon genes, mobile genes in animal and plant, have, to some extent, unique nucleotide sequences, whose information has enabled research on wider applications of transposons. However, enough elucidation has not been demonstrated. Additionally, a nucleotide sequence, assigned to a putative transposon gene has been found in a mutated rice induced by γ-irradiation (Tetsuya Nakazaki et al., "Polymorphic insertion of transposon-like sequence in mutable slender-granule gene slg locus" Japanese Society of Breeding $100^{th}$ Conference, Autumn meeting, 2001, October).

Problems to be Solved by the Invention:

The inventors discovered an inverted repeated sequence characteristic to transposon genes in rice genome nucleotide sequence under investigation. Examining various tests on the possible transposon nucleotide sequence, the inventors confirmed that the nucleotide sequence is ascribed to a transposon gene (nonautonomous transposon).

Furthermore, the inventors discovered autonomous transposon genes on the basis of the nonautonomous transposon gene. Moreover, the inventors identified transposase genes, which enable to transpose the transposon gene.

Means of Solving the Problems:

The inventors, starting from chromosome No. 1, examined long terminal repeats (LTR) in rice genome sequence, which is registered seriatim in database. The inventors noticed a LTR on the clone, accession number AP002843, as shown in Table 1, investigated the sequence in detail and discovered the inverted repeat sequence characteristic to a transposon gene at the site of $144459^{th}$–$144473^{rd}$ and $144874^{th}$–$144888^{th}$ bases at adjacent downstream of LTR (FIG. 1, SEQ ID NO: 6). As disclosing in the example shown later, the inventors confirmed that the nucleotide sequence (SEQ ID NO: 1) located between the inverted repeats is a nonautonomous transposon gene, markedly transposable by such artificial treatment as anther culture.

TABLE 1

| AP002843 Oryza sativa genomic DNA, chromosome 1, PA | | | | |
|---|---|---|---|---|
| ACCESSION | AP002843 | NCBI SRS Genome-Net | | |
| ORGANISM | Oryza sativa | NCBI SRS | | |
| LOCUS | AP002843 148762 bp | DNA | PLN | 26-JAN-2001 |
| FEATURES | Location/Qualifiers | | | |
| source | 1..148762 | | | |
| | /chromosome="1" | | | |
| | /clone="P0407B12" | | | |
| | /cultivar="Nipponbare" | | | |
| | /organism="Oryza sativa" | | | |
| | /sequenced_mol="DNA" | | | |
| LTR | 139482..139690 | | | |
| | /note="5' LTR" | | | |
| CDS | 139739..144052 | | | |
| | /gene="P0407B12.28" | | | |
| | /note="probably inactive due to frameshifts in CDS" | | | |
| | /note="pseudogene, similar to Oryza longistaminata probable gag/pol polyprotein U72725" | | | |
| | /pseudo | | | |
| LTR | 144047..144255 | | | |
| | /note="3' LTR" | | | |
| CDS | join(144653..144692, 145148..145311) | | | |
| | /codon_start=1 | | | |
| | /gene="P0407B12.29" | | | |
| | /note="hypothetical protein" | | | |
| | /protein_id="BAB17191.1" | | | |
| | /translation="MRRSHGGGGRKRSVPSSSHPEKKAIDRIKREDAGRRAGRVSLVQ PLAAFPATDGGGGGLARLLRWW" | | | |
| | (SEQ. ID NO: 28) | | | |

Then, the inventors searched for homologous sequences using the nonautonomous transposon gene (SEQ ID NO: 1) by Blast search. Most of the results of the search lead to the nonautonomous transposon gene (SEQ ID NO: 1) itself, but additionally, accession numbers AP004236 and AP003968, which were expected as transposon genes, were found. Comparing the nucleotide sequence of AP004236 and AP003968, the inventors found that these are cloned on chromosome No. 6 and are the sequence of the identical overlapped region.

Therefore, the homology between $1^{st}$–$253^{rd}$ bases of the nonautonomous transposon gene (SEQ ID NO: 1) and $89360^{th}$–$89612^{nd}$ bases of AP004236 was 252/253 (99%) and that between $254^{th}$–$430^{th}$ bases of the nonautonomous transposon gene (SEQ ID NO: 1) and $94524^{th}$–$94700^{th}$ bases of AP004236 was 177/177 (100%). They are well-conserved sequences.

Both nonautonomous transposon gene (SEQ ID NO: 1, 430 bp) and the transposon (SEQ ID NO: 2, 5341 bp) have inverted repeats of 15 bp and TTA and TAA are recognized and inserted. Open Reading Frame (ORF) was searched on the basis of SEQ ID NO: 2 (5341 bp) and two kinds of putative ORFI and ORFII were obtained.

Open Reading Frame (ORF) was searched on the basis of Sequence Number 2 (5341 bp) and two kinds of putative ORFI and ORFII were obtained.

The structure of the transposon gene comprising nucleotide sequence of SEQ ID NO: 2 is shown in the upper diagram of FIG. 9. The nonautonomous transposon gene (SEQ ID NO: 1, 430 bp) is located at $1^{st}$–$253^{rd}$ and at $5165^{th}$–$5341^{st}$ bases, ORFI is located at $1526^{th}$–$1914^{th}$ bases and at $1939^{th}$–$2663^{rd}$ bases and ORFII is located at $3190^{th}$–$4557^{th}$ bases.

Furthermore, to obtain similar genes to the gene comprising nucleotide sequence of SEQ ID NO: 2, the inventors performed homological searches using nucleotide sequence of SEQ ID NO: 2 as Query (DNA for homological search) of Blast search and found accession numbers AP004753 (chromosome No. 2) and AP003714 (chromosome No. 6) as well as the sequence of SEQ ID NO: 2 itself. These two clones have the identical nucleotide sequence (SEQ ID NO: 3) and located on different chromosomes (several copies). Since the nucleotide sequence is present also in indica (a cultivar of rice), the gene must be conserved in many cultivars, from japonica to indica. The nucleotide sequence of SEQ ID NO: 3 (5166 bp) has inverted repeats, as the sequence of SEQ ID NO: 2 has, and TAA (3 bp) was also recognized and inserted.

Open Reading Frame (ORF) was searched on the basis of the sequence of SEQ ID NO: 3 and ORFI and ORFII were obtained which may code two kinds of proteins. The structure of transposon gene comprising nucleotide sequence of SEQ ID NO: 3 is shown in the lower diagram of FIG. 9. The nonautonomous transposon gene (SEQ ID NO: 1, 430 bp) is located at $1^{st}$–$170^{th}$ and at $5092^{nd}$–$5166^{th}$ bases, however, the homological nucleotide sequence to the nonautonomous transposon gene (SEQ ID NO: 1, 430 bp) is disappeared in the middle. ORFI is located at $1630^{th}$–$2652^{nd}$ bases and ORFII is located at $2959^{th}$–$4407^{th}$ bases. The nucleotide sequence of SEQ ID NO: 3 was compared between japonica (AP004753 and AP003714) and indica (Scaffold6962) and the homology of more than 90% was confirmed as shown in FIG. 10. Additionally, the inventors examined the mutation frequency of nonautonomous transposon gene (SEQ ID NO: 1, 430 bp) in indica, and confirmed that the sequence homology was more than 95% as shown in FIG. 11.

The inventors have no idea on the function of ORFI in SEQ ID NOS 2 and 3, for the moment.

To examine whether ORFII encodes transposase (transposition enzyme) or not, the inventors checked whether the amino acid sequence of ORFII shares a conservative region with that of known transposase gene. The amino acid sequences of ORFII in SEQ ID NO: 2 and in SEQ ID NO: 3 are shown as SEQ ID NOS 4 and 5, respectively. The alignment of amino acid sequences of these two ORFII (SEQ ID NOS 4 and 5) is shown in FIG. 12 and the homology of these sequences was more than 75% (77%). These two amino acid sequences have DXG/AF/F motif and YREK motif (SEQ ID NO: 39) (Q. H. Le, K. Turcotte and T. Bureau, Genetics 158: 1081–1088 (2001)), then it is concluded that thee belong to IS transposase family.

Also, the homology of the nucleotide sequences of ORFII in SEQ ID NO: 2 and that in SEQ ID NO: 3 was more than 75% (79.3%).

Therefore, the present invention is a transposon gene of rice consisting of a nucleotide sequence which is at least 95% homological to SEQ ID NO: 1. The DNA being at least 95% homological to SEQ ID NO: 1 is considered to be functional as nonautonomous transposon, which is transposable by anther culture or by the treatment with chemical agents. Also, the present invention is the transposon gene of rice, wherein enhancers or promoters are inserted.

Furthermore, the present invention is the transposon gene of rice, whose nucleotide sequence is at least 90% homological to the nucleotide sequence of SEQ ID NO: 2 or 3. The DNA being at least 90% homological to the nucleotide sequence of SEQ ID NO: 2 or 3 is considered to be functional as an autonomous transposon gene, which is transposable by anther culture or by the treatment with chemical agents.

Also, the present invention is the transposase gene of rice, whose DNA being at least 75% homological to the nucleotide sequence of $3190^{th}$–$4557^{th}$ bases off SEQ ID NO: 2 or the nucleotide sequence of $2959^{th}$–$4407^{th}$ bases of SEQ ID NO: 3. The DNA being at least 75% homological to these nucleotide sequences is considered to be functional as the gene, which enables transpose the transposons.

Also, the present invention is the transposase gene encoding a protein consisting of an amino acid sequence of SEQ ID NO: 4 or 5 or an amino acid sequence wherein one or several amino acids are deleted, substituted or added in said amino acid sequence. Also, the transposase could be a transposon gene of rice, whose amino acids sequence is at least 75% homological to SEQ ID NO: 4 or 5.

Moreover, the present invention is the transposase gene encoding this protein. Also, the present invention is the plasmid containing any one of said transposon genes. Still furthermore, the present invention is the plasmid containing promoters and anyone of said transposase genes. Such binary vector as Ti plasmid and pBI-121 plasmid can be used for the purpose. 35S promoter of cauliflower mosaic virus, heat shock promoter, chemotaxis promoter and others can be used for the purpose of this invention. There are no restrictions on the method of incorporation of promoters and said genomes and general method of genetic engineering can be applied.

Also, the present invention is the transfomants, wherein any of said transposon genes are transduced. Preferably, plants, especially, rice, barley, wheat or maize are used as the host. To transform these plants, using general method of genetic engineering, we can insert these genomes into said plasmid and transform the plants.

Still moreover, the present invention is the transfomants, wherein promoters and said transposase genes are transduced. Other transposon genes can be transduced, if necessary. Said promoters can be used for the present purpose. Preferably, plants, especially, barely, wheat or maize are used as the host. To transform these plants, using general method of genetic engineering, we can insert said genomes into said plasmid and transform the plants.

Also, the present invention is the method for transposing any of said transposon genes, comprising subjecting said transformants to anther culture or treating any of the transformants with a chemical agent.

Furthermore, the present invention is the plant or the seed, which is transformed by the transposition of said transposon genes by any one of said methods. Preferably, rice or barley, a vicinal species of rice, wheat or maize is used as the plant.

Also, the present invention is a method for determining the integrated region of transposon gene, which comprises the steps of transposing any one of said transposon gene by any one of the above methods, extracting DNA from the plant obtained by the previous step, digesting said DNA by a restriction enzyme with no cutting sites inside the transposon gene, ligating said DNA fragments obtained by the previous step, conducting PCR for said DNA fragments obtained by the previous step, and determining the nucleotide sequence of said PCR products obtained by the previous steps. The primers of said PCR involve the oligonucleotides, which comprises 10 consecutive bases, preferably 10~20 consecutive bases, more preferably 10~15 consecutive bases in the nucleotide sequence from the 5'-end of SEQ ID NO: 1; and the oligonucleotide, which comprises 10 consecutive bases, preferably 10~20 consecutive bases, more preferably 10~15 consecutive bases in the nucleotide sequence from the 3'-end of SEQ ID NO: 1, or the oligonucleotides, comprising the nucleotide sequences complementary to said sequences. Since the origonucleotide comprising 10~15 consecutive bases from the 5'-end of the nucleotide sequence overlaps with that comprising 10~15 consecutive bases in the nucleotide sequence from the 3'-end of that of SEQ ID NO: 1, we can use single kind of primer, if the oligonucleotide bases comprises less than 15 consecutive bases. In other words, in this case, we can use the oligonucleotide comprising 10~15 consecutive bases in the nucleotide sequence from the 5'-end of SEQ ID NO: 1 or the oligonucleotides complementary to said nucleotide sequences as the PCR primer. In this way, identification of the integration site of the transposon enables to find the disrupted genomes.

BRIEF DESCRIPTION OF THE DRAWINGS

FIG. 1 shows a part (SEQ. ID NO: 6) of genomic nucleotide sequence of accession number AP002843. The inverted repeated sequences characteristic to the transposon gene are located at the positions of 144459 to 144473 and 144874 to 144888, immediately after LTR.

FIG. 2 shows the result of agarose gel electrophoresis of PCR products of the DNA region (Accession Number AP002843) containing the transposon DNA from four cultivars of rice mature leaves (Example 2). An approximately 850 bp band in Nihonbare shows that a transposon gene (430 bp) is inserted in the region. While, approximately 420 bp bands for Koshihikari, Hitomebore and Yamahoushi show that transposon genes are not inserted.

FIG. 8 shows the base sequence of 4 clones, from which the transposon gene (430 bp) is deleted (SEQ. ID NOS.: 36, 30, 31, 32 and 33, respectively in order of appearance).

FIG. 9 shows the structure of the transposon genes with nucleotide sequences of SEQ. ID NOS.: 2 and 3.

FIG. 10 shows the homology of nucleotide sequence between japonica (AP004753 and AP003714) and indica (Scaffold6962) in the region of SEQ. ID NO.: 3.

FIG. 11 shows the mutation frequency of transposon gene (SEQ. ID NO: 1, 430 bp) in indica.

FIG. 12 shows the alignment of amino acid sequence of ORFII in SEQ. ID NO.: 2 and in SEQ. ID NO.: 3. The homology of their sequence is more than 75% (77.8%; in the figure, the homological amino acids are shown by *) and both sequences have DXG/AF/F motif and YREK motif (SEQ ID NO: 39). The upper line shows the amino acid sequence of SEQ ID NO: 4 (correspond to ORF II of SEQ. ID NO.: 2), and the lower line shows that of SEQ. ID NO.: 5 (correspond to ORF II of SEQ. ID NO.: 3).

FIG. 13—right shows the result of agarose gel electrophoresis of the DNA region (accession number AP004236) containing the transposon DNA in various calli derived from seeds of Nihonbare (Comparative Example 2).

FIG. 17 shows the nucleotide sequence of such size of DNA fragment SEQ. ID NO.: 34 that is suggestive of deletion of the nonautonomous transposon gene located in L02 gene locus (SEQ ID NOS 37). The nucleotide sequence of the nonautonomous transposon gene (SEQ. ID NO.: 1) is deleted.

FIG. 18 shows the nucleotide sequence of such size of DNA fragment SEQ. ID NO.: 35 that is suggestive of deletion of the nonautonomous transposon gene located in L06 gene locus (SEQ ID NO: 38). The nucleotide sequence of the nonautonomous transposon gene (SEQ. ID NO.: 1) is deleted.

FEATURE OF EMBODIMENT

Figure 3:
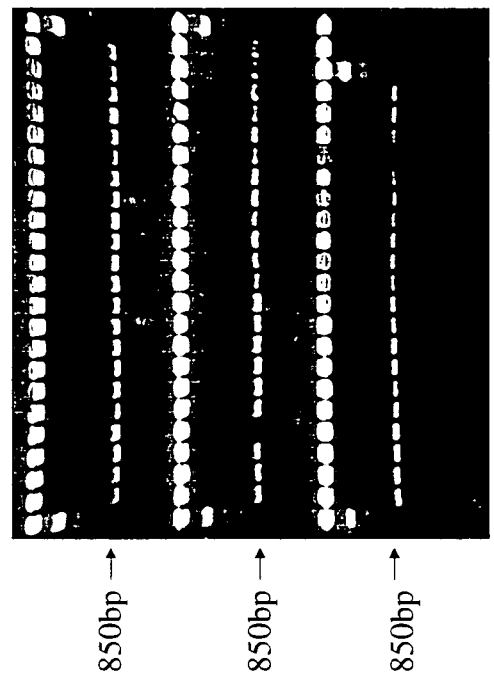
FIG. 3 shows the result of agarose gel electrophoresis of PCR products of the DNA region (Accession Number AP002843) containing transposon DNA in calli derived from Nihonbare seeds (Comparative Example 1).

First of all, this invention is the nonautonomous transposon gene (SEQ. ID NO.: 1) of rice with the DNA size of 430 bp. This transposon gene has terminal inverted repeats with the size of 15 bp and has a symmetric structure with 215 bp (CT).

Then, two kinds of transposon genes (SEQ. ID NOS.: 2 and 3) encode transposases (SEQ ID NOS 4 and 5) and are autonomous transposon genes.

An autonomous transposon gene is characteristic in encoding transposases, is mobile and induces transposition of a nonautonomous transposon gene. Whereas, a nonautonomous transposon gene is lacking a transposase, is not mobile and needs a help of autonomous transposon gene to transpose. The comparison structurally of autonomous transposon gene with nonautonomous gene, demonstrated the characteristics that the nucleotide sequences of both genes are homological and are well conserved except the DNA region deleted.

The plants carrying the transposon of this invention; or the plants transformed by the transposon of this invention; or the plants carrying the transposase gene of this invention; or the plants transformed by the transposase gene of this invention enable to transpose the transposons of this invention by activation, induced by irradiation; induced by treatment with chemical agents; or induced by anther culture. Since transposons can be greatly activated by these methods, transposition of an artificial transposon takes place easily.

Treatment with chemical agents is carried out by treating seeds, leaves, roots, and stems of axillary buds of a plant such as rice; or by treating calli derived from them, with chemical agents. For example, the treatment of these plants with 5-azacytidine or 5-azadeoxycytidine is generally carried out by transplanting them on solid or liquid medium containing 0.01~5 mM, preferably 0.05~2 mM of these chemical agents. As used therein, callus means a cellular mass, formed by dedifferentiation of differentiated plant organs, obtained by culturing plant organs such as roots, leaves or stems in an appropriate medium supplemented with appropriate concentrations of auxin or cytokinin. This cellular mass is not differentiated and has totipotency in differentiation. Totipotency of differentiation means that the cellular mass can regenerate new organs such as buds or roots. For example, a single leaf can produce hundreds of clones, mediated by callus.

Anther culture is a kind of method to produce doubled haploid breeding. Anthers are taken out from the tip of stamens of rice and are cultured in a medium supplemented mainly with such hormone as auxin together with such polyploidy-iducing chemicals as colchicine and others. Since haploid cells can easily turn to diploid, it is easy to obtain diploid cells from anthers, i.e. haploid cells with a set of genes. Anther-derived callus of rice spontaneously doubles the number of chromosome, resulting in doubled haploid breeds, during prolonged culture period. A homozygote seed, a mutant plant, can be obtained by regeneration culture of the callus. We mainly, for regeneration culture, used the medium supplemented with such hormone as cytokinin.

The disrupted transposon gene, due to the insertion of transposed transposon gene, could be identified using the probe prepared by PCR using a primer set derived from appropriate two different nucleotide sequences in the transposon gene. An examination of correlation between transoformed rice mutant and its gene enables to clarify the function of the gene.

It is a challenging object to identify easily a disrupted gene by a transposon tagging system. A lot of methods are known to determine the exact integration site of a transposon such as transposon display. However, they usually accompany complicated handlings. We inventors established a simple method using inverse PCR. In this method, an important key step is the design of PCR primers in the interior of the transposon gene. DNA is isolated from plants, digested by a restriction enzyme (we used AluI in this example), which has no cutting sites in the internal region of the transposon gene, and ligated intramolecularly to circularize the DNA by a ligase. On the basis of the obtained circular DNA as a template, we performed a PCR reaction using a primer set, which originally pointed away each other but which, after ligation, will prime towards one another around the circular DNA. The designed primer set, which consists of the oligonucleotide comprising at least 10 consecutive bases from the 5'-end of the nucleotide sequence of SEQ. ID NO.: 1, and the oligonucleotide comprising at least 10 consecutive bases from the 3'-end of the nucleotide sequence of SEQ. ID NO.: 1, preferably in the internal region of terminal inverted repeats (15 consecutive bases from both the 5'- and 3'-end of SEQ. ID NO.: 1); or oligonucleotides comprising the nucleotide sequence complementary to them, can be used for the inverse PCR. DNA sequencing of the obtained PCR products clarifies the integration site of the transposon gene. As an example of application of the nonautonomous transposon (SEQ. ID NO.: 1), integration of enhancers or promoters into the internal region of the nonautonomous transposon enables to induce transposition of these enhancers or promoters together with the nonautonomous transposon. More specifically, transducing the genome, wherein enhancers or promoters are inserted, into rice or other plants; or culturing of anthers; or treating them with chemical agents; or inducing the transposition of the genome, we can demonstrate active expression other genomes flanking to the integration site of the transposed genome and, as a result, we can get a lot of mutants with gain-of-function.

As promoters and enhancers for said example, we can use the 35S promoter of cauliflower mosaic virus and four sets in series of enhancer region (at positions −90 to −440 in the sequence) in the 35S promoter, respectively. There are no restrictions on the integration site for the enhancer except the internal region of the inverted repeats of the genome with SEQ. ID NO.: 1. Also on the integration site of the promoters, there are no restrictions except the internal region of the inverted repeats of the genome with SEQ. ID NO.: 1 and except nonexistence of methionine in the adjacent downstream region of the integrated site. Preferably, both enhancers and promoters are integrated at position around 250 of SEQ. ID NO.: 1, if there are no troubles in the transposition of the transposon. To integrate enhancers and promoters, we can use the restriction enzyme site, which divides in two the nucleotide sequence of the genome of SEQ. ID NO.: 1 or use the cloning sites prepared by PCR.

EFFECTS OF THE INVENTION

The present invention, for the first time, demonstrated mobile transposon genes of rice, since previously these rice genes have not been known. Furthermore, inventors confirmed, by such simple method as anther culture and others, that nonautonomous transposon genes are transposable. In other words, we succeeded to provide a new method to transpose artificially a nonautonomous transposon gene.

Also in the examples, we demonstrated that nonautonomous transposon genes are deletable by such artificial treatment as anther culture and others. Furthermore, we directly confirmed the genetic locus, wherein nonautonomous transposon genes are inserted. Since we found artificially transposable transposon genes, we succeeded, for the first time, in preparing an artificial system of transposon tagging in rice.

Furthermore, the present invention demonstrated autonomous transposon genes (SEQ. ID NOS.: 2 and 3) of rice and transposase genes included in the genomes. The inventors confirmed, by such simple method as anther culture or drug treatment, that the transposon gene could be transposed in rice, wherein the autonomous transposon gene was transduced. In other words, the present invention provides a method to transform these plants easily and artificially, whereby the autonomous transposon genes or transposase genes are transduced artificially into rice and other plants.

The autonomous transposon genes of this invention can be used as a source of random mutagens and can produce a system of transposon tagging in rice and other plants. This invention can be used to produce several dozen of plant breeds, wherein the transposons are randomly transposed. Since spontaneous transposition in growing natural plants are very rare, efficient induction of transposition can be achieved in callus derived from induced anthers in plant tissue culture or callus derived from seeds treated with 5-azacytidine. It is possible to induce efficient transposition in plants other than rice, wherein the autonomous transposon genes of this invention are transduced by a transformation method. The mutated plants thus obtained can be analyzed by genetic analysis or by reverse genetic analysis.

Genetic analysis is a method to isolate a causal gene from phenotypes of mutants. If a transposon gene of this invention is linked to a phenotype of mutants, the causal gene of the phenotype can easily be isolated by the help of tagging (the transposon).

For example, if one wishes to look for a rice breed tolerant to salt, one may examine the tolerance of rice grown from seeds from the system of transposon tagging and may find the desired rice.

Reverse genetic analysis is a method to isolate a mutant, wherein genetic function is lost, from a pool of wild host. If a desired gene of a plant is tagged by the transposon, the phenotype related to the gene should be mutated. DNA is isolated from various mutants and a genomic library of a tagged genome is prepared. We can request a transposon tagging system from a public stock centers. Screening the transposon tagging system, we can isolate tagged desired gene-transposon ensemble by PCR.

Recent progress of genome project made it cyclopaedically possible to prepare a set of mutants corresponding to entire genomes of rice and to prepare a database for the site of insertion of transposon corresponding to the mutants. User can order seeds of desired mutant by searching the database.

The following examples illustrate this invention, however, it is not intended to limit the scope of the invention.

EXAMPLE 1

DNA was extracted from mature leaves of Nihonbare, a rice cultivar (Kikuchi et al. (1998) Plant Biotechnology 15: 45–48). To amplify the central DNA region between both inverted terminal repeats located on both ends of transposon DNA, we used the oligonucleotide comprising the sequence of SEQ. ID NO.: 7 as PCR primers. We carried out PCR using GENEAMP9600® system (ABI Co.). Each reaction mixture (100 µl) contained 200 ng of DNA, 2.5 units of TAKARA EX TAQ® (Takara Co.), 10 µl of 10×Ex Taq buffer, 8 µl of dNTP mixture (2.5 mM each dNTP) and 200 pmol of primers. Each cycle of the polymerase reaction consisted of a denaturation step at 94° C. for 30 sec, an annealing step at 55° C. for 1 min and an extension step at 72° C. for 12 min. This cycle was repeated 35 times. After the reaction, DNA was separated on 1% SEAKEM GTG agarose® (FMC Co.). The amplified DNA fragment with approximately 450 bp was recovered from the gel and it was subcloned in plasmid pCRII-TOPO using TA CLONING KIT® (In Vitrogen). The nucleotide sequence of the obtained clone was determined using 310 DNA SEQUENCER® (ABI Co.). The nucleotide sequence thus determined was shown as SEQ. ID NO.: 1, consisted of 430 bp.

EXAMPLE 2

DNA was isolated from leaves of 4 cultivars of rice, Nihonbare, Koshihikari, Hitomebore and Yamahoushi. To amplify the DNA region containing the transposon DNA (accession number AP002843) by PCR, we used the oligonucleotides comprising the sequences of SEQ. ID NOS.: 8 and 9 as PCR primers. Each reaction mixture (100 µl) contained 200 ng of DNA, 2.5 units of AMPLITAQ GOLD® (ABICo.), 10 µl of GENEAMP10®×PCR buffer (contains 15 mM MgCl$_2$), 10 µl of GENE AMP MIXTURE® (2 mM each dNTP) and 200 pmol of primers. Each cycle of the polymerase reaction consisted of a denaturation step at 96° C. for 30 sec, an annealing step at 55° C. for 1 min and an extension step at 72° C. for 1 min. This cycle was repeated 35 times. After the reaction, DNA was separated on 2% LO3 AGAROSE® (Takara Co.). FIG. 2 shows the result of the agarose gel electrophoresis. The DNA band of approximately 850 bp was found only for Nihonbare (lane 2). The DNA band of approximately 850 bp indicates the DNA fragment, including the transposon gene (430 bp) of SEQ. ID NO.: 1 as described in example 1. While, DNA fragments of 420 bp, not including the transposon gene, were found for Koshihikari, Hitomebore and Yamahoushi. The fact that the gene comprising the sequence of SEQ. ID NO.: 1 was found only for Nihonbare among these rice cultivars suggests that the gene may function as a transposable element.

COMPARATIVE EXAMPLE 1

The seeds of Nihonbare were sterilized in 3% sodium hypochlorite solution for 15 to 30 min, washed with sterilized water, inoculated on a 90×20 mm of Petri dish (Iwaki Co.) containing 20~30 ml of media at the rate of 9 seeds per dish and subjected to growth culture under light for 24 h at 30° C. We used a solid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 0.3 g of casamino acids (DIFCO), 0.1 g of myo-inositol (Sigma Co.), 2.878 g proline (Wako), 30 g of sucrose (Wako), 2 g of GELRITE® (Wako) in 1 L of medium. On the $10^{th}$ day of inductive culture, the calli derived from induced seeds were transplanted to a 90×20 mm of Petri dish (Iwaki Co.) containing 20~30 ml of medium and subjected to growth culture under light for 24 h at 30° C. We used a solid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 0.3 g of casamino acids (DIFCO), 0.1 g of myo-inositol (Sigma Co.), 2.878 g proline (Wako), 30 g of sucrose (Wako), 2 g of GELRITE® (Wako) in 1 L of medium.

DNA was extracted from calluses derived from seeds in growth culture for two weeks. To amplify the DNA region containing the transposon DNA by PCR, we used the oligonucleotides comprising the sequences of SEQ. ID NOS.: 8 and 9 as PCR primers as described in Example 2. Each reaction mixture (100 μl) contained 200 ng of DNA, 2.5 units of GOLD AMPLITAQ GOLD® (ABI Co.), 10 μl of GENEAMP10®×PCR buffer (contains 15 mM $MgCl_2$), 10 μl of GENE AMP MIXTURE® (2 mM each dNTP) and 200 pmol of primers. Each cycle of the polymerase reaction consisted of a denaturation step at 96° C. for 30 sec, an annealing step at 55° C. for 1 min and an extension step at 72° C. for 1 min. This cycle was repeated 35 times. After the reaction, DNA was separated on 2% LO3 AGAROSE® (Takara Co.). FIG. 3 shows the result of the agarose gel electrophoresis. Only a single DNA band of approximately 850 bp was found. The DNA band of approximately 850 bp indicates the DNA fragment, including the transposon gene. The expected DNA band of 420 bp, wherein transposon gene was deleted, could not be found. The probability that the band of size of approximately 420 bp is found was 0 callus per 64 calli (0%). Therefore, it was confirmed that transposon genes were not mobile in seed (scutellum)-derived calli.

EXAMPLE 3

Spikes of Nihonbare were harvested at pre-emergence, kept in cold treatment for 10 days at 10° C., sterilized in 1% sodium hypochlorite solution for 1 min and washed with sterilized water. Then, anthers were picked out from the floret, seeded in a 35×10 mm Petri dish (CORNING Co.) containing 3 ml of liquid medium at the rate of 50 anthers per dish and subjected to induction culture under light for 24 h at 30° C. Used was a liquid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 30 g of sucrose (Wako) in 1 L of medium. After 3~4 weeks of inductive culture, the calli derived from induced anthers were transplanted to a 90×20 mm of Petri dish (Iwaki Co.) containing 20~30 ml of medium and subjected to growth culture under light for 24 h at 30° C. We used a solid medium consisting of 4 g of CHU (N6) BASAL SALT MIXTURE® (Sigma Co.), 1 ml of MS VITAMIN SOLUTION® (Sigma Co.), 2 ml of α-naphthalene acetic acid solution (Sigma Co.), 2 ml of kinetin solution (Sigma Co.), 3 g of casamino acids (DIFCO), 30 g of sucrose (Wako), 2 g of GELRITE® (Wako) in 1 L of medium.

Figure 4:
FIG. 4 shows the result of agarose gel electrophoresis of PCR products of the DNA region (Accession Number AP002843) containing transposon DNA in various calli derived from Nihonbare anthers (Example 3). The DNA bands of approximately 420 bp demonstrate that the transposon gene is deleted.

DNA was extracted from calli derived from anthers in growth culture for 2 weeks. To amplify the DNA region containing the transposon DNA by PCR, we used the oligonucleotides comprising the sequences of SEQ. ID NOS.: 8 and 9 as PCR primers as described in example 2. Each reaction mixture (100 μl) contained 200 ng of DNA, 2.5 units of AMPLITAQ GOLD® (ABI Co.), 10 μl of GENEAMP10®×PCR buffer (contains 15 mM $MgCl_2$), 10 μl of GENE AMP MIXTUR® (2 mM each dNTP) and 200 pmol of primers. Each cycle of the polymerase reaction consisted of a denaturation step at 96° C. for 30 sec, an annealing step at 55° C. for 1 min and an extension step at 72° C. for 1 min. This cycle was repeated 35 times. After the reaction, DNA was separated using 2% LO3 AGAROSE® (Takara Co.). FIG. 4 shows the result of the agarose gel electrophoresis. As shown in FIG. 4, two DNA bands of approximately 850 bp and 420 bp were obtained. The DNA band of approximately 850 bp indicates the DNA band including a transposon gene. While, the band of approximately 420 bp indicates that transposon genes were deleted. The probability that the DNA band of approximately 420 bp is observed was 11 calli per 64 calli (17.2%).

Since the DNA bands of approximately 420 bp, indicating the deletion of the transposon gene, was the PCR products from anther derived calli in this example, the amplified DNA fragments (approximately 420 bp, N=5) were recovered from the gel and subcloned into plasmid PCRII-TOPO USING TA CLONING KIT® (In Vitrogen). The nucleotide sequence of 5 clones thus obtained was determined by 310 DNA SEQUENCER® (ABI Co.). The alignment of these nucleotide sequences clarified the absence of the transposon gene sequence in these 5 clones (data not shown). Therefore, the inventors confirmed the deletion of the transposon gene on the basis of nucleotide sequences.

In comparative example 1, the transposon gene in scutellum (seed) derived cell cultures was not mobile, however, in this example, the transposon gene in anther derived cell cultures was mobile highly frequently.

EXAMPLE 4

Spikes of Nihonbare were harvested at pre-emergence, kept in cold treatment for 10 days at 10° C., sterilized in 1% sodium hypochlorite solution for 1 min and washed with sterilized water. Then, anthers were picked out from the floret, seeded in a 35×10 mm Petri dish (CORNING Co.) containing 3 ml of liquid medium at the rate of 50 anthers per dish and subjected to induction culture under light for 24 h at 30° C. We used a liquid medium consisting of 4 g of CHU(N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 30 g of sucrose (Wako) in 1 L of medium. After 3~4 weeks of inductive culture, the calli derived from induced anthers were transplanted to a 90×20 mm of Petri dish (Iwaki Co.) containing 20~30 ml of medium and subjected to growth culture under light for 24 h at 30° C. We used a solid medium consisting of 4 g of CHU (N6) BASAL SALT MIXTURE® (Sigma Co.), 1 ml of MS VITAMIN SOLUTION® (Sigma Co.), 2 ml of α-naphthalene acetic acid solution (Sigma Co.), 2 ml of kinetin solution (Sigma Co.), 3 g of casamino acids (DIFCO), 30 g of sucrose (Wako), 2 g of GELRITE® (Wako) in 1 L of medium. The anther derive calli in growth culture for two weeks were transplanted in a 90×20 mm Petri dish (Iwaki Co.) with 20~30 ml of medium and were cultured for regeneration under light for 24 h, at 30° C. We used a solid medium consisting of 4.3 g of MS BASAL SALT MIXTURE® (Gibcobrl Co.), 1 ml of MS VITAMIN SOLUTION® (Sigma Co.), 10 ml of 6-benzylamino-purine solution (Sigma Co.), 2 ml of α-naphthalene acetic acid solution (Sigma Co.), 2 g of casamino acids (DIFCO), 30 g of sorbitol (Wako), 30 g of sucrose (Wako), 2 g of GEL-RITE® (Wako) in 1 L of medium. The regenerated plant, in regeneration culture for 3~4 weeks, was transplanted in a growth culture and, when it was grown up, transferred to the soil. As a growth medium, we used a solid medium consisting of 4.3 g of MS BASAL SALT MIXTURE® (Gibcobrl. Co.), 1 ml of MS VITAMIN SOLUTION® (Sigma Co.), 30 g of sucrose (Wako) and 2 g of GELRITE® (Wako) in 1 L of medium.

Figure 5:
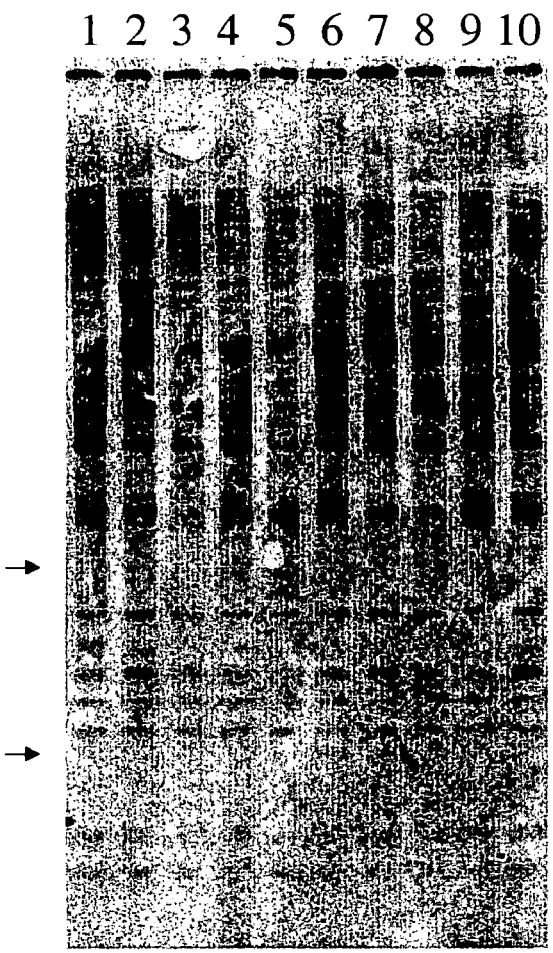
FIG. 5 shows the result of agarose gel electrophoresis of DNA from various calli derived from Nihonbare anthers (Example 4). Lane 1 shows control Nihonbare and Lanes 2~10 show plant regenerated from anther derived-calli. DNA bands were detected using a probe comprising a part of the transposon nucleotide sequence. Lanes 2 and 6 show new bands (indicated by arrowheads), which were not found in control Nihonbare.

DNA was extracted from 9 young seedlings, regenerated from anther-derived calli by CTBA method. The extracted DNA was digested with a restriction enzyme HindIII, separated on 0.8% LO3 AGAROSE® (Takara Co.) gel electrophoresis and transferred to a Nylon membrane (HybondN+) (Amersham Co.) by alkaline blotting. The DIG LUMINES-CENCE DNA DETECTION KIT® (Roche Co.) was used for Southern hybridization. The PCR DIG PROBE SYN-THESIS KIT® (Roche Co.) was used for preparation of probes. To amplify the internal DNA region containing the transposon DNA by PCR, we used the oligonucleotides comprising the sequences of SEQ. ID NOS.: 10 and 11 (both sequences are located inside the SEQ. ID NO.: 1 (transposon gene)) as PCR primers as described in example 2. FIG. 5 shows the result of the agarose gel electrophoresis. As shown in FIG. 5, two new bands (indicated by arrows), which were not observed in control Nihonbare, were found in Lanes 2 and 6. These two bands show that the transposon gene was inserted in these seedlings and then disrupted.

Figure 6:
FIG. 6 is a photograph of a phenotypic transformer found in regenerated rice in example 4. The leaves of the rice are curly and short.

On the basis of the present example, it was clarified that the transposon gene was inserted to new genetic loci. Furthermore, an example of morphological mutation (the relevant gene is not determined) was found in regenerated rice as shown in FIG. 6 and the example may suggest that genes related to morphology was disrupted by the insertion of the transposon gene.

EXAMPLE 5

Seeds of Nihonbare were sterilized in 3% sodium hypochlorite solution for 15~30 min, washed with sterilized water, inoculated on a 90×20 mm of Petri dish (Iwaki Co.) containing 20~30 ml of media at the rate of 9 seeds per dish and subjected to induction culture under light for 24 h at 30° C. We used a solid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 0.3 g of casamino acids (DIFCO), 0.1 g of myo-inositol (Sigma Co.), 2.878 g proline (Wako), 30 g of sucrose (Wako), 2 g of GELRITE® (Wako) in 1 L of medium.

After several days, calli were started forming from scutellum inside rice seeds and changed to cream-colored ones with 5 mm length on the 10$^{th}$ day of culture. The creamy-colored calli with 5 mm length were transplanted to growth media supplemented with 5-azacytidine (Sigma Co.) at either 0 mM, 0.01 mM, 0.03 mM, 0.05 mM, 0.1 mM or 0.3 mM, respectively, and subjected to growth culture under light for 24 h at 30° C. We used a solid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 0.3 g of casamino acids (DIFCO), 0.1 g of myo-inositol (Sigma Co.), 2.878 g proline (Wako), 30 g of sucrose (Wako), 2 g of GELRITE® (Wako) in 1 L of medium.

DNA was extracted by DNEASY PLANT MINI KIT® (QIAGEN) from calli derived from seeds in growth culture for 2 weeks. To amplify the DNA region containing the transposon DNA by PCR, and oligonucleotides comprising the sequences of SEQ. ID NOS.: 12 and 13 as PCR primers were used.

As PCR reaction mixture, HOTSTARTAQ MASTER MIX KIT® (QIAGEN) was used.

Each cycle of the polymerase reaction consisted of a denaturation step at 96° C. for 30 sec, an annealing step at 55° C. for 1 min and an extension step at 72° C. for 1 min. This cycle was repeated 45 times. After the reaction, DNA was separated on 2% LO3 AGAROSE® (Takara Co.).

Figure 7:
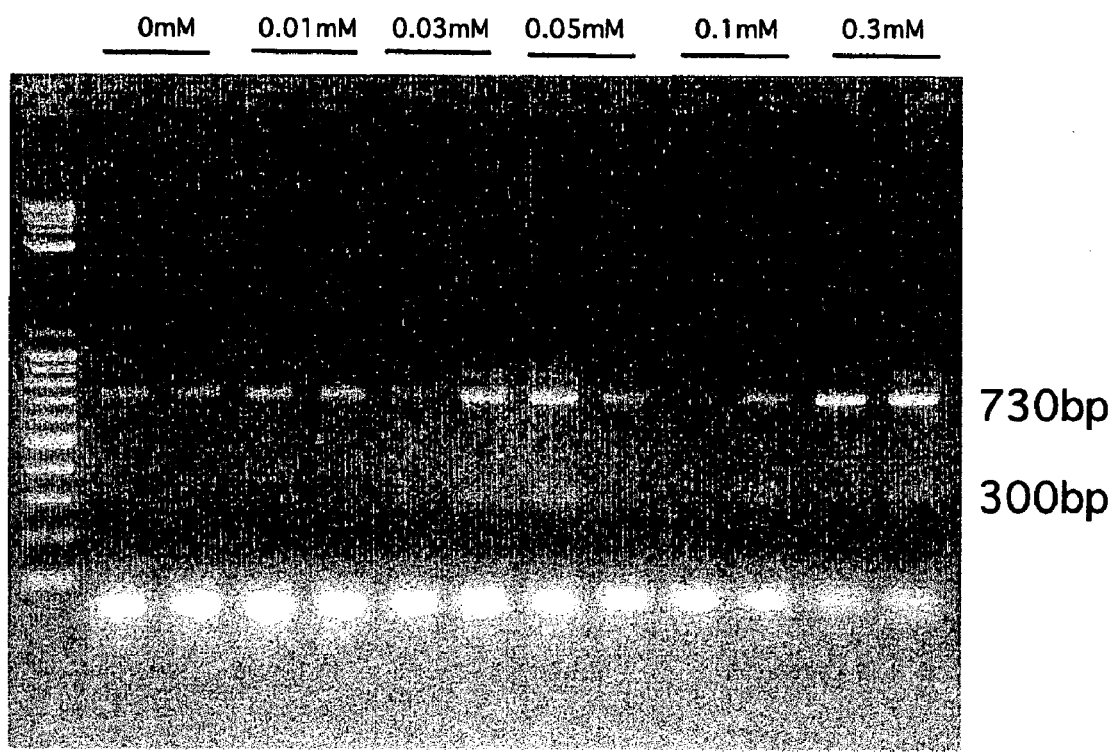
FIG. 7 shows the result of agarose gel electrophoresis of PCR products of the DNA region containing the transposon DNA from various calli derived from Nihonbare seeds (Example 5). The numbers on the upper margin indicate concentrations of 5-azacytidine. The DNA bands of approximately 300 bp demonstrate that the transposon gene (430 bp) is deleted.

Two DNA bands of approximately 730 bp and 300 bp were observed for calli cultured supplemented with 0.03 mM–0.3 mM of 5-azacytidine (FIG. 7). The DNA band of approximately 730 bp indicates the DNA band including a transposon gene. While, the DNA band of approximately 300 bp indicates the DNA bands not including the transposon gene (430 bp).

These DNA fragments (300 bp) were recovered from the gel and subcloned into plasmid PCRII-TOPO USING TA CLONING KIT® (InVitrogen) The nucleotide sequence of 4 clones thus obtained was determined by 310 DNA SEQUENCER® (ABI Co.). The nucleotide sequences of 4 clones were subjected to a multiple alignment as shown in FIG. 8. No transposon gene sequence was found in these 4 clones.

This example showed that the transposition of the transposon gene of this invention could be induced even for seed-derived calli by means of 5-azacytidine, a demethylating agent. Based on this result, it can be expected that several hundreds of clones transposed by this transposon gene could be obtained from a single seed.

EXAMPLE 6

Spikes of Nihonbare were harvested at pre-emergence, kept in cold treatment for 10 days at 10° C., sterilized in 1% sodium hypochlorite solution for 1 min and washed with sterilized water. Then, anthers were picked out from the floret, seeded in a 35×10 mm Petri dish (CORNING Co.) containing 3 ml of liquid medium at the rate of 50 anthers per dish and subjected to induction culture under light for 24 h at 30° C. A liquid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 30 g of sucrose (Wako) in 1 L of medium was used. After 3~4 weeks of inductive culture, the calli derived from induced anthers were transplanted to a 90×20 mm of Petri dish (Iwaki Co.) containing 20~30 ml of medium and subjected to growth culture under light for 24 h at 30° C. We used a solid medium consisting of 4 g of CHU (N6) BASAL SALT MIXTURE® (Sigma Co.), 1 ml of MS VITAMIN SOLUTION® (Sigma Co.), 2 ml of α-naphthalene acetic acid solution (Sigma Co.), 2 ml of kinetin solution (Sigma Co.), 3 g of casamino acids (DIFCO), 30 g of sucrose (Wako), 2 g of GELRITE® (Wako) in 1 L of medium.

DNA was extracted from calli derived from anthers in growth culture for 2 weeks (Kikuchi et al. (1998) Plant Biotechnology 15: 45–48). To amplify the DNA region containing the transposon DNA by PCR, we used the oligonucleotides comprising the sequences of SEQ. ID NO.: 14 ($88933^{rd}$–$88962^{nd}$ bases of AP004236) and SEQ. ID NO.: 15 ($95545^{th}$–$95574^{th}$ bases of AP004236) as PCR primers. Each reaction mixture (100 μl) contained 200 ng of DNA, 2.5 units of TAKARA LA TAQ® (Takara Co.), 10 μl of 10×LA PCR BUFFER II®, 6 μl of 25 mM $MgCl_2$, 8 μl of dNTP mixture (2.5 mM each dNTP) and 100 pmol of primers.

Figure 13:
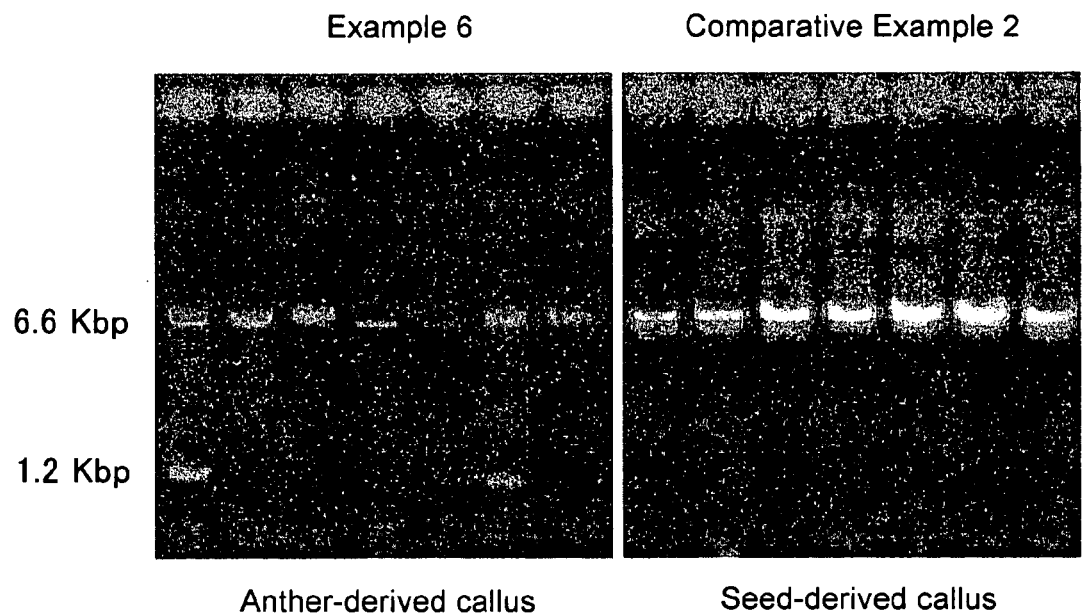
FIG. 13—left shows the result of agarose gel electrophoresis of PCR products of the DNA region (accession number AP004236) containing transposon DNA in various calli derived from anthers of Nihonbare (Example 6). The DNA bands of 1.2 kbp indicate deletion of the transposon gene.

Each cycle of the polymerase reaction consisted of a denaturation step at 94° C. for 30 sec and an extension step at 68° C. for 12 min. This cycle was repeated 35 times. After the reaction, DNA was separated on 0.8% LO3 AGAROSE® (Takara Co.) gel electrophoresis. The DNA band of approximately 6.6 kbp indicates the DNA band including the transposon gene (5341 bp) of this invention. Since the size of the transposon of this invention is approximately 5.4 kbp, the DNA band of approximately 1.2 kbp could be expected when this transposon gene is deleted. A DNA band of approximately 1.2 kbp was obtained in this example (FIG. 13). These results show that the transposon gene is mobile in anther-derived calli. The probability, that the DNA band of approximately 1.2 kbp was observed in calli, was three calli per 64 calli (4.7%). This example proved that the MITE of rice with the nucleotide sequence of SEQ. ID NO.: 2 was mobile in anther-derived calli.

COMPARATIVE EXAMPLE 2

Seeds of Nihonbare, a rice cultivar, were sterilized in 3% sodium hypochlorite solution for 15~30 min, washed with sterilized water, inoculated on a 90×20 mm of Petri dish (Iwaki Co.) containing 20~30 ml of media at the rate of 9 seeds per dish and subjected to induction culture under light for 24 h at 30° C. Used was a solid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 0.3 g of casamino acids (DIFCO), 0.1 g of myo-inositol (Sigma Co.), 2.878 g proline (Wako), 30 g of sucrose (Wako), 2 g of GELRITE® (Wako) in 1 L of medium. On the $10^{th}$ day of inductive culture, the calli derived from induced seeds were transplanted to a 90×20 mm of Petri dish (Iwaki Co.) containing 20~30 ml of medium and subjected to growth culture under light for 24 h at 30° C. Used was a solid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 0.3 g of casamino acids (DIFCO), 0.1 g of myo-inositol (Sigma Co.), 2.878 g proline (Wako), 30 g of sucrose (Wako), 2 g of GELRITE® (Wako) in 1 L of medium. DNA was extracted from calli derived from seeds in growth culture for two weeks (Kikuchi et al. (1998) Plant Biotechnology 15: 45–48). To amplify the DNA region containing the transposon DNA by PCR, we used the oligonucleotides comprising the sequences of SEQ. ID NOS.: 14 and 15 as PCR primers. Each reaction mixture (100 μl) contained 200 ng of DNA, 2.5 units of TAKARA LA TAQ® (Takara Co.), 10 μl of 10×LA PCR BUFFER II®, 6 μl of 25 mM $MgCl_2$, 8 μl of dNTP mixture (2.5 mM each dNTP) and 100 pmol of primers. Each cycle of the polymerase reaction consisted of a denaturation step at 94° C. for 30 sec and an extension step at 68° C. for 12 min. This cycle was repeated 35 times. After the reaction, DNA was separated on 0.8% LO3 AGAROSE® (Takara Co.) gel electrophoresis. A single DNA band of approximately 6.6 kbp, but not a band of approximately 1.2 kbp, was observed for all calli samples from seeds (FIG. 13). The result implied that transposon genes were not mobile in seed derived-calli. The probability that the DNA band of approximately 1.2 kbp was observed in seed-derived callus is 0 callus per 64 calli (0%).

EXAMPLE 7

In this example, to look for a cultivar, wherein the autonomous transposon gene (SEQ. ID NO.: 2) is not included and to clarify whether there is a difference in the efficiency of the transposition of a nonautonomous transposon gene between calli with the autonomous transposon gene (SEQ. ID NO.: 2) and those without the gene, we induced anther-derived callus from cultivars not including autonomous transposon gene (SEQ. ID NO.: 2) and checked the efficiency of the transposition of a nonautonomous transposon gene.

Figure 14:
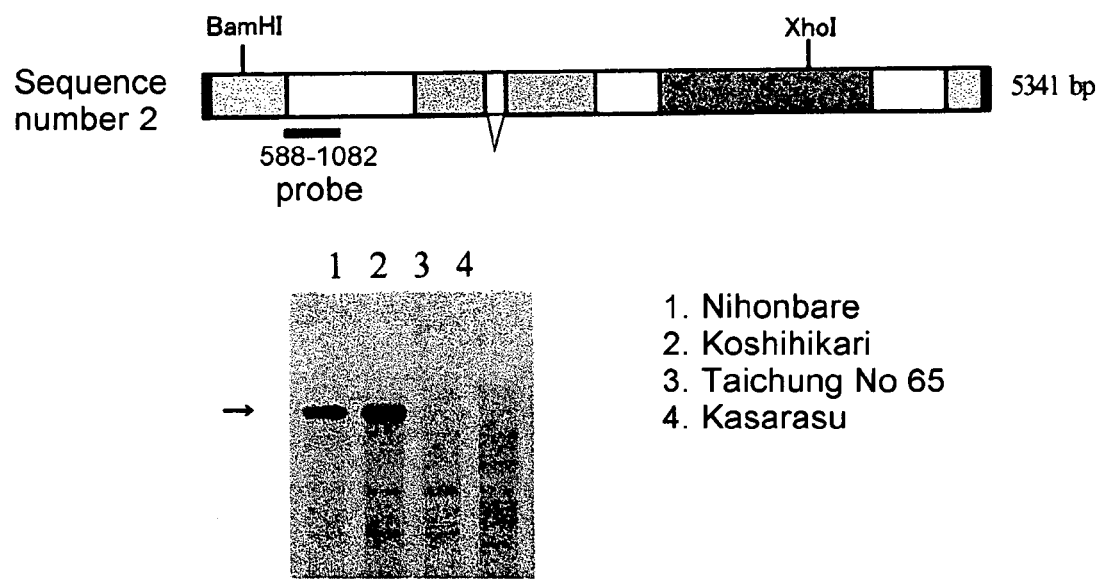
FIG. 14 is the result of gel electrophoresis of DNA, which shows presence or absence of the autonomous transposon gene (SEQ ID NO: 2; shown on the upper margin of the photograph) in various rice cultivars (Example 7). A DNA band (shown by an arrow) indicating the presence of the autonomous transposon gene (SEQ. ID NO.: 2) was found in Nihonbare (lane 1) and in Koshihikari (lane 2), while, the DNA band was absent in Taichung No. 65 (lane 3) and in Kasarasu (lane 4).

DNA was isolated by CTAB method from leaves of 4 kinds of rice cultivars, Nihonbare, Koshihikari, Taichung No. 65 and Kasarasu. The isolated DNA was digested by a restriction enzyme, HindIII, separated by 1.0% LO3 AGAROSE® gel electrophoresis, transferred to a Nylon membrane (HybondN+, Amersham Co.) by an alkaline blotting and detected by DIG LUMINESCENCE DNA DETECTION KIT® (Roche Co.) using Southern hybridization. The PCR DIG PROBE SYNTHESIS KIT® (Roche Co.) was used for preparation of probes. To amplify the DNA region specific to the autonomous transposon gene by PCR, we used the oligonucleotides comprising the sequences of SEQ. ID NOS.: 16 and 17 as PCR primers. The result of Southern hybridization shows that one copy of autonomous transposon gene exists in both Nihonbare and Koshihikari, but not in Taichung No. 65 and Kasarasu (FIG. 14).

Then, we induced callus derived from anthers of Taichung No. 65 and examined whether nonautonomous tranposon gene (SEQ. ID NO.: 1) was transposed.

Spikes of Taichung No. 65 were harvested from the head spout before forming the spikes, kept in cold treatment for 10 days at 10° C., sterilized in 1% sodium hypochlorite solution for 1 min and washed with sterilized water. Then, anthers were picked out from the caryopsis, seeded in a 35×10 mm Petri dish (CORNING Co.) containing 3 ml of liquid medium at the rate of 50 anthers per dish and subjected to induction culture under light for 24 h at 30° C. Used was a liquid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 30 g of sucrose (Wako) in 1 L of medium. After 3~4 weeks of inductive culture, the calli derived from induced anthers were transplanted to a 90×20 mm of Petri dish (Iwaki Co.) containing 20~30 ml of medium and subjected to growth culture under light for 24 h at 30° C. Used was a solid medium consisting of 4 g of CHU (N6) BASAL SALT MIXTURES (Sigma Co.), 1 ml of MS VITAMIN SOLUTION® (Sigma Co.), 2 ml of α-naphthalene acetic acid solution (Sigma Co.), 2 ml of kinetin solution (Sigma Co.), 3 g of casamino acids (DIFCO), 30 g of sucrose (Wako), 2 g of GELRITE® (Wako) in 1 L of medium.

DNA was extracted from calli derived from anthers in growth culture for 2 weeks according to the method described (Kikuchi et al. (1998) Plant Biotechnology 15: 45–48). To amplify the DNA region specific to the autonomous transposon gene by PCR, we used the oligonucleotides comprising the sequences of SEQ. ID NOS.: 18 and 19 (L02), SEQ. ID NOS.: 20 and 21 (L06) and SEQ. ID NOS.: 22 and 23 (L07) as PCR primers. Each reaction mixture (100 µl) contained 200 ng of DNA, 2.5 units of AMPLITAQ GOLD® (ABI Co.), 10 µl of GeneAmp10×PCR buffer (contains 15 mM MgCl$_2$), 10 µl of GENE AMP MIXTURE® (2 mM each dNTP) and 200 pmol of primers. Each cycle of the polymerase reaction consisted of a denaturation step at 96° C. for 30 sec, an annealing step at 55° C. for 1 min and an extension step at 72° C. for 1 min. This cycle was repeated 35 times. After the reaction, DNA was separated on 2% LO3 AGAROSE® (Takara Co.). The results show that there are no transpositions of the nonaoutonomous transposon gene, located in L02, L06 and L07 loci, in Taichung N. 65, not carrying the autonomous transposon gene (SEQ. ID NO.: 1) (Table 2, the first line). However the nonautonomous transposon gene transposed in high frequency at 10.9–31.3% in anther-derived callus of Nihonbare, which carries the autonomous transposon gene (SEQ. ID NO.: 2), as shown in the following comparative Example 3.

TABLE 2

|  | L02 | L06 | L07 |
|---|---|---|---|
| Anther-derived callus | 0/64 | 0/64 | 0/64 |
| Gene-transduced anther-derived callus | 2/38 5.3% | 1/38 2.6% | 0/38 0% |

COMPARATIVE EXAMPLE 3

Spikes of Nihonbare were harvested at pre-emergence, kept in cold treatment for 10 days at 10° C., sterilized in 1% sodium hypochlorite solution for 1 min and washed with sterilized water. Then, anthers were picked out from the floret, seeded in a 35×10 mm Petri dish (CORNING Co.) containing 3 ml of liquid medium at the rate of 50 anthers per dish and subjected to induction culture under light for 24 h at 30° C. A liquid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 30 g of sucrose (Wako) in 1 L of medium was used. After 3–4 weeks of inductive culture, the calli derived from induced anthers were transplanted to a 90×20 mm of Petri dish (Iwaki Co.) containing 20–30 ml of medium and subjected to growth culture under light for 24 h at 30° C. Used was a solid medium consisting of 4 g of CHU (N6) BASAL SALT MIXTURE® (Sigma Co.), 1 ml of MS VITAMIN SOLUTION® (Sigma Co.), 2 ml of α-naphthalene acetic acid solution (Sigma Co.), 2 ml of kinetin solution (Sigma Co.), 3 g of casamino acids (DIFCO), 30 g of sucrose (Wako), 2 g of GELRITE® (Wako) in 1 L of medium. DNA was extracted from calli derived from anthers in growth culture for 2 weeks. To amplify the DNA region containing the transposon DNA by PCR, we used the oligonucleotides comprising the sequences of SEQ. ID NOS.: 5 and 1 as PCR primers as described in example 7. Each reaction mixture (100 µl) contained 200 ng of DNA, 2.5 units of AMPLITAQ GOLD® (ABI Co.), 10 µl of GeneAmp10×PCR buffer (contains 15 mM MgCl$_2$), 10 µl of GENE AMP MIXTURE® (2 mM each dNTP) and 200 pmol of primers. Each cycle of the polymerase reaction consisted of a denaturation step at 96° C. for 30 sec, an annealing step at 55° C. for 1 min and an extension step at 72° C. for 1 min. This cycle was repeated 35 times. After the reaction, DNA was separated using 2% LO3 AGAROSE® (Takara Co.). We obtained the result that there are two DNA bands of approximately 850 bp and 420 bp. The DNA band of approximately 850 bp indicates the DNA band including a transposon gene. While, the band of approximately 420 bp indicates that transposon genes were deleted. The probability, that the DNA band of approximately 420 bp is observed, was 11 calli per 64 calli (17.2%).

EXAMPLE 8

In this example, the DNA region including the autonomous transposon gene (SEQ. ID NO.: 2) was isolated, transduced to a cultivar (Taichung No. 65), which does not include the autonomous transposon gene (SEQ. ID NO.: 2), and examined the possibility of transposition of nonautonomous transposon gene (SEQ. ID NO.: 1) in this cultivar.

To amplify the DNA region including the autonomous transposon gene (SEQ. ID NO.: 2) from Nihonbare, a cultivar of rice, we designed two primer nucleotide sequences, SEQ. ID NOS.: 24 and 25, whose sequences are located at the adjacent upstream and downstream, respectively, of the target DNA region (SEQ. ID NO.: 2) for the PCR reaction. We synthesized the origonucleotides of the sequences of SEQ. ID NOS.: 24 and 25 and used them as primers. DNA was isolated from leaves of Nihonbare by CTAB method. Each reaction mixture (100 µl) contained 200 ng of DNA, 2.5 units of TAKARA LA TAQ® (Takara Co.), 10 µl of 10×LA PCR BUFFER II®, 6 µl of 25 mM MgCl$_2$, 8 µl of dNTP mixture (2.5 mM each dNTP) and 100 pmol of primers. Each cycle of the polymerase reaction consisted of a denaturation step at 94° C. for 30 sec and an extension step at 68° C. for 12 min. This cycle was repeated 35 times. After the reaction, DNA was separated on 0.8% LO3 AGAROSE® (Takara Co.) gel electrophoresis. We obtained the DNA band of approximately 6.6 kbp, including the autonomous transposon gene. The DNA fragment (approximately 6.6 kbp) was recovered from gel slices, subcloned into plasmid PCRII-TOPO USING TA CLONING KIT® (In Vitrogen), cut out using the multicloning sites (ApaI and KpnI) in pCRII-TOPO using TA CLONING KIT®, subcloned to a binary vector, which contains a selectable marker gene, hygromycin resistant gene, and could be used for plant infection, and transduced to Agrobacteria EHA101 by electroporation. On three days before the infection of the Agrobacteria to anther-derived callus, the Agrobacteria were streaked onto AB medium containing kanamycin (Wako) and hygromycin (Wako).

Then, mediated by the *Agrobacterium*, the DNA fragments (approximately 6.6 kbp), wherein the autonomous tranposon gene (SEQ. ID NO.: 2) was included, were transduced to the anther-derived calli of Taichung No. 65, a rice cultivar.

Spikes of Taichung No. 65 were harvested at pre-emergence, kept in cold treatment for 10 days at 10° C., sterilized in 1% sodium hypochlorite solution for 1 min and washed with sterilized water. Then, anthers were picked out from the floret, seeded in a 35×10 mm Petri dish (CORNING Co.) containing 3 ml of liquid medium at the rate of 50 anthers per dish and subjected to induction culture under light for 24 h at 30° C. A liquid medium consisting of 4 g of CHU (N6) BASAL SALT MIXTURE® (Sigma Co.), 1 ml of MS VITAMIN SOLUTION® (Sigma Co.), 2 mg of 2,4- dichloro-phenoxyacetic acid (Sigma Co.), 30 g of sucrose (Wako) in 1 L of medium was used. After 3~4 weeks of inductive culture, the calli derived from induced anthers were transplanted to a 90×20 mm of Petri dish (Iwaki Co.) containing 20~30 ml of medium and subjected to growth culture under light for 24 h at 30° C. A solid medium consisting of 4 g of CHU (N6) BASAL SALT MIXTURE® (Sigma Co.), 1 ml of MS VITAMIN SOLUTION® (Sigma Co.), 2 ml of α-naphthalene acetic acid solution (Sigma Co.), 2 ml of kinetin solution (Sigma Co.), 3 g of casamino acids (DIFCO), 30 g of sucrose (Wako), 2 g of GELRITE® (Wako) in 1 L of medium was used.

The Agrobacteria were infected to anther-derived calli originated from Taichung No. 65, at 2 weeks of growth culture in growth medium. The Agrobacteria, streaked onto the surface of AB medium and kept for three days, were scraped by a spatula, mixed with AAM medium (25 ml) supplemented with 10 mg/L acetosyringone. The mixed medium with the *Agrobacterium* for infection was kept in a Petri dish (IWAKI). The calli, in wire cage, derived from anther in growth culture for 2 weeks was immersed into the mixed medium for infection for 2 min. After the immersion, the mesh cage was put on a sterilized paper towel and removed the excess medium. The callus was put on a filter paper on a symbiotic medium by a forceps and cultured at 28° C. for 3 days under dark, sealed by a surgical tape. The symbiotic medium used was a solid medium containing 4 g of CHU (N6) BASAL SALT MIXTURE® (Sigma Co.), 1 ml of MS VITAMIN SOLUTION® (Sigma Co.), 30 g of Sucrose (Wako), 10 g of Glucose (Wako), 2 mg of 2,4-dichloro-phenoxyacetic acid (Sigma Co.), 2 g of GELRITE® (Wako) and 10 mg of acetosyringone in 1 L of medium. After symbiotic culture for 3 days, the callus was added to an Erlenmeyer flask with 100 ml of sterilized water, shaken well and the water was discarded. After washing with sterilized water several times and with washing solution supplemented with 500 mg/ml of carbenisillin, the callus was transplanted on Petri dish at the rate of 9 calli/dish, sealed by a surgical tape and was cultured under light at 25° C. for a month. As a selection medium, used was a solid medium consisting of 4 g of CHU (N6) BASAL SALT MIXTURE® (Sigma Co.), 1 ml of MS Vitamine Solution (Sigma Co.), 30 g of sucrose (Wako), 0.3 g of casamino acids (DIFCO), 2.878 g of proline (ICN), 0.1 g of mio-inositol (Sigma Co.), 2 mg of 2,4-dichloro-phenoxyacetic acid (Sigma Co.), 500 mg of hygromycin (Wako), 50 mg of carbenicillin (Wako), 2 g of GELRITE® (Wako) in 1 L of medium.

Then, we examined the possible transduction of the autonomous transposon gene of Nihonbare and the possible transposition of the nonautonomous transposon gene (SEQ. ID NO.: 1) in hygromycin-resistant calli, grown in a selection medium for 3~4 weeks after seeded on the medium.

DNA was isolated from the resistant calli according to the method described (Kikuchi et al. (1998) Plant Biotechnology 15: 45–48). To amplify the DNA region including the autonomous transposon gene (SEQ. ID NO.: 2), we used the oligonucleotides comprising the sequences of SEQ. ID NOS.: 24 and 25, located at the adjacent upstream and down stream, respectively, of the target DNA region (SEQ. ID NO.: 2), as primers.

Figure 15:
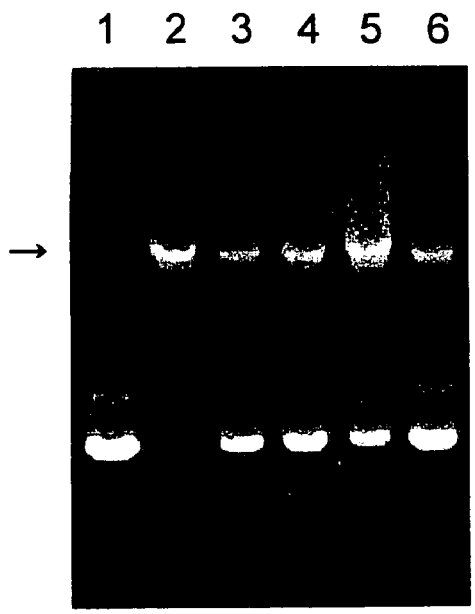
FIG. 15 is the result of gel electrophoresis of DNA from calli derived from anthers of Taichung No. 65, wherein the autonomous transposon gene from Nihonbare (SEQ. ID NO.: 2) was transduced (example 8). The DNA bands (shown by an arrow) indicating that the autonomous transposon gene (SEQ. ID NO.: 2) was absent in original Taichung No. 65 (lane 2), but present in calli derived from anthers of Taichung No. 65 (lanes 3 to 6), wherein the autonomous transposon gene (SEQ. ID NO.: 2) was transduced.

Each reaction mixture (100 μl) contained 200 ng of DNA, 2.5 units of TAKARA LA TAQ® (Takara Co.), 10 μl of 10×LA PCR BUFFER II®, 6 μl of 25 mM MgCl$_2$, 8 μl of dNTP mixture (2.5 mM each dNTP) and 100 pmol of primers. Each cycle of the polymerase reaction consisted of a denaturation step at 94° C. for 30 sec and an extension step at 68° C. for 12 min. This cycle was repeated 35 times. After the reaction the PCR products were separated on 0.8% LO3 AGAROSE® (Takara Co.) gel electrophoresis. As shown the results in FIG. 15, we confirmed the transduction of the autonomous transposon gene of Nihonbare in hygromycin-resistant calli from Taichung No. 65.

Figure 16:
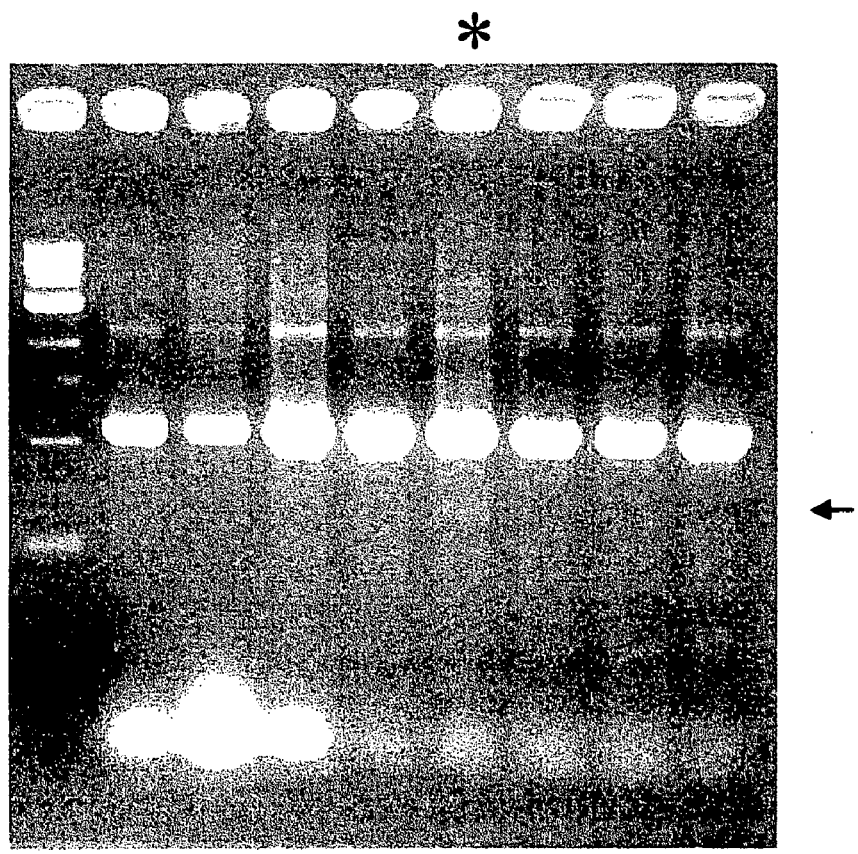
FIG. 16 is the result of gel electrophoresis of PCR products of the DNA region containing the nonautonomous transposon gene of calli derived from anthers of Taichung No. 65, wherein the autonomous transposon gene from Nihonbare (SEQ. ID NO.: 2, Example 8) was transduced. On L06 gene locus, such size of DNA band (shown by an arrow) that is suggestive of deletion of the nonautonomous transposon gene, was observed.

Then to amplify the DNA region including the nonautonomous transposon gene by PCR, we used the oligonucleotides comprising the sequences of SEQ. ID NOS.: 18 and 19 (L02), SEQ. ID NO.: 20 and 21 (L06) and SEQ. ID NOS.: 22 and 23 (L07) as primers. As PCR reaction mixture, we used HOTSTARTAQ MASTER MIX KIT® (QIAGEN). Each cycle of the polymerase reaction consisted of a denaturation step at 96° C. for 30 sec, an annealing step at 55° C. for 1 min and an extension step at 72° C. for 2 min. This cycle was repeated 45 times. After the reaction, DNA was separated on 2% LO3 AGAROSE® (Takara Co.). We examined the possibility of deletion of the nonautonomous transposon gene for 38 calli, wherein the autonomous transposon gene was transduced, and obtained a DNA band (shown by an arrow), suggestive of deletion of the nonautonomous transposon gene in L06 gene locus (FIG. 16). The frequency of deletion of the nonautonomous transposon gene in L02, L06 and L07 gene loci was around 0~5.3% (Table 2, the $2^{nd}$ line).

The DNA fragments suggestive of the deletion of nonautonomous transposon gene in L02 and L06 gene loci were recovered from the gel and subcloned into plasmids pCRII-TOPO using TA CLONING KIT® using a TA cloning kit (In Vitrogen). The nucleotide sequences of the clones obtained were determined by 310 DNA SEQUENCER® (ABI Co.). There was no nonautonomous transposon gene in these clones (FIGS. 17 and 18).

These result show that transposition of the nonautonomous transposon gene was induced in anther-derived calli originated from Taichung No. 65, wherein the autonomous transposon gene of Nihonbare was transduced.

On the basis of these results, we can conclude that the transposon gene expressed by SEQ. ID NO.: 2 not only transposes autonomously in anther-derived calli but also regulates the transposition of the nonautonomous transposon gene.

EXAMPLE 9

In this example, we examined the transposition activity of the nucleotide sequence of SEQ. ID NO.: 3 in anther-derived calli and in scutellum-derived calli treated with 5-azacytidine.

Spikes of Nihonbare were harvested at pre-emergence, kept in cold treatment for 10 days at 10° C., sterilized in 1% sodium hypochlorite solution for 1 min and washed with sterilized water. Then, anthers were picked out from the floret, seeded in a 35×10 mm Petri dish (CORNING Co.) containing 3 ml of liquid medium at the rate of 50 anthers per dish and subjected to induction culture under light for 24 h at 30° C. Used was a liquid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 30 g of sucrose (Wako) in 1 L of medium. After 3~4 weeks of inductive culture, the calli derived from induced anthers were transplanted to a 90×20 mm of Petri dish (Iwaki Co.) containing 20~30 ml of medium and subjected to growth culture under light for 24 h at 30° C. Used was a solid medium consisting of 4 g of CHU (N6) BASAL SALT MIXTURE® (Sigma Co.), 1 ml of MS VITAMIN SOLU- TION® (Sigma Co.), 2 ml of α-naphthalene acetic acid solution (Sigma Co.), 2 ml of kinetin solution (Sigma Co.), 3 g of casamino acids (DIFCO), 30 g of sucrose (Wako), 2 g of GELRITE® (Wako) in 1 L of medium. DNA was extracted from calli derived from anthers in growth culture for 2 weeks according to the method described (Kikuchi et al. (1998) Plant Biotechnology 15: 45–48).

Seeds of Nihonbare, a rice cultivar, were sterilized in 3% sodium hypochlorite solution for 15~30 min, washed with sterilized water, inoculated on a 90×20 mm of Petri dish (Iwaki Co.) with 20~30 ml of media at the rate of 9 seeds per dish and subjected to induction culture under light for 24 h at 30° C. Used was a solid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 0.3 g of casamino acids (DIFCO), 0.1 g of myo-inositol (Sigma Co.), 2.878 g proline (Wako), 30 g of sucrose (Wako), 2 g of GELRITE® (Wako) in 1 L of medium. On the 10$^{th}$ day of inductive culture, the calli derived from induced seeds were transferred to a growth medium supplemented with 5-azacytidine (Sigma) at 0 mM, 0.1 mM or 0.5 mM and were subjected to growth culture under light for 24 h at 30° C. Used was a solid medium consisting of 4 g of CHU (N6) BASAL SALT MIXTURE® (Sigma Co.), 1 ml of MS VITAMIN SOLUTION® (Sigma Co.), 2 mg of 2,4-dichloro-phenoxyacetic acid (Sigma Co.), 0.3 g of casamino acids (DIFCO), 0.1 g of myo-inositol (Sigma Co.), 2.878 g proline (Wako), 30 g of sucrose (Wako), 2 g of GELRITE® (Wako) in 1 L of medium. DNA was extracted from calli derived from seeds in growth culture for two weeks by DNEASY PLANT MINI KIT® (Qiagen).

To amplify the DNA region containing the transposon DNA by PCR, we used the oligonucleotides comprising the sequences of SEQ. ID NOS.: 26 and 27 as PCR primers. Each reaction mixture (100 μl) contained 200 ng of DNA, 2.5 units of TAKARA LA TAQ® (Takara Co.), 10 μl of 10×LA PCR bufferII, 6 □l of 25 mM MgCl$_2$, 8 μl of dNTP Mixture (2.5 mM each dNTP) and 100 pmol of primers. Each cycle of the polymerase reaction consisted of a denaturation step at 94° C. for 30 sec and an extension step at 68° C. for 12 min. This cycle was repeated 35 times. After the reaction, PCR products were separated on 0.8% LO3 AGAROSE® (Takara Co.) gel electrophoresis.

It was found that the transposon gene with the nucleotide sequence of SEQ. ID NO.: 3 was not transposed in anther-derived calli and in scutellum-derived calli, but high frequency of transposition was taken place in scutellum-derived calli treated with 5-azacytidine (Table 3).

TABLE 3

|  | The frequency of deletion |
|---|---|
| Anther-derived callus (Nihonbare) | 0/64 (0%) |
| Scutellum-derived callus (Nihonbare) | 0/64 (0%) |
| 0 mM 5-azacytidine | 0/8 (0%) |
| 0.1 mM 5-azacytidine | 2/8 (25%) |
| 0.5 mM 5-azacytidine | 7/8 (87.5%) |

The transposon gene with the nucleotide sequence of SEQ. ID NO.: 3 has the structure of an autonomous transposon gene with a coding sequence of a transposase, can be activated by the treatment with 5-azacytidine and may control the transposition of nonautonomous transposon gene (SEQ. ID NO.: 1).

EXAMPLE 10

DNA was extracted from mature leaves of Kasarasu, a cultivar of rice, by DNEASY PLANT MINI KIT® (QIAGEN). To amplify the DNA region adjacent to the inserted transposon gene by PCR, we used an inverse PCR method. We used the oligonucleotide comprising the sequence (5'-CCATTGTGACTGGCC-3') (SEQ. ID NO.: 29) of 15 bases from the 5'-end of SEQ. ID NO.: 1 as a primer for inverse PCR. GENEAMP9600 SYSTEM® (ABI Co.) was used for PCR. HOTSTARTAQ MASTER MIX KIT® (QIAGEN) was used for PCR reaction solution. Each cycle of the polymerase reaction consisted of a denaturation step at 96° C. for 30 sec, an annealing step at 44~58° C. for 1 min and an extension step at 72° C. for 1 min. This cycle was repeated 45 times. After the reaction, PCR products were separated on 2% LO3 AGAROSE® (Takara Co.) gel electrophoresis. The amplified DNA fragments were subcloned into a plasmid PCRII-TOPO USING TA CLONING KIT® (In Vitrogen). The nucleotide sequence of the obtained clone was determined by 310 DNA SEQUENCER® (ABI Co.).

The invention claimed is:

1. A method for transposing the transposon gene of rice comprising a nucleotide sequence at least 95% identical to SEQ ID NO: 1 comprising,
   culturing anthers of rice, or
   treating seeds, leaves, roots, or stems of axillary buds of rice, or a callus derived from them of with 5 azacytidine or 5-azadeoxycytidine.

2. A method for determining the integration site of a transposon comprising a nucleotide sequence at least 95% identical to SEQ ID NO:1, said method comprising the steps of a) amplifying a segment of genomic DNA utilizing a primer comprising at least 15 contiguous nucleotides of SEQ ID NO:1 for inverse PCR, b) isolating the amplified DNA, and c) determining the sequence of the genomic plant DNA flanking said transposon, thereby determining the integration site of said transposon.

3. The method of claim 2, wherein the plant species is selected from the group consisting of rice, barley, wheat and maize.

* * * * *

UNITED STATES PATENT AND TRADEMARK OFFICE
CERTIFICATE OF CORRECTION

PATENT NO.        : 7,132,587 B2                                         Page 1 of 1
APPLICATION NO.   : 10/494944
DATED             : November 7, 2006
INVENTOR(S)       : Kazuhiro Kikuchi et al.

It is certified that error appears in the above-identified patent and that said Letters Patent is hereby corrected as shown below:

Title Page, item (73) Assignee should read: --Japan Science and Technology Agency--

Signed and Sealed this

Twenty-ninth Day of May, 2007

JON W. DUDAS
*Director of the United States Patent and Trademark Office*

SEQUENCE LISTING

```
<160> NUMBER OF SEQ ID NOS: 27

<210> SEQ ID NO 1
<211> LENGTH: 430
<212> TYPE: DNA
<213> ORGANISM: Oryza sativa

<400> SEQUENCE: 1
ggccagtcac aatgggggtt tcactggtgt gtcatgcaca tttaataggg gtaagactga      60
ataaaaaatg attatttgca tgaaatgggg atgagagaga aggaaagagt ttcatcctgg     120
tgaaactcgt cagcgtcgtt tccaagtcct cggtaacaga gtgaaacccc cgttgaggcc     180
gattcgtttc attcaccgga tctcttgcgt ccgcctccgc cgtgcgacct ccgcattctc     240
```

-continued

| ccgcgccgcg ccggattttg ggtacaaatg atcccagcaa cttgtatcaa ttaaatgctt | 300 |
| tgcttagtct tggaaacgtc aaagtgaaac ccctccactg tggggattgt ttcataaaag | 360 |
| atttcatttg agagaagatg gtataatatt ttgggtagcc gtgcaatgac actagccatt | 420 |
| gtgactggcc | 430 |

<210> SEQ ID NO 2
<211> LENGTH: 5341
<212> TYPE: DNA
<213> ORGANISM: Oryza sativa

<400> SEQUENCE: 2

| ggccagtcac aatggaggtt tcactggtgt gtcatgcaca tttaataggg gtaagactga | 60 |
| ataaaaaatg attatttgca tgaaatgggg atgagagaga aggaaagagt ttcatcctgg | 120 |
| tgaaactcgt cagcgtcgtt tccaagtcct cggtaacaga gtgaaacccc cgttgaggcc | 180 |
| gattcgtttc attaccggga tctcttgcgt ccgcctccgc cgtgcgacct ccgcattctc | 240 |
| ccgcgccgcg ccgcgccacg cctccttccc gcgtgaacat tcctccttcc cgcgcgagcg | 300 |
| attccaccat ctcccccgtc cggcgcctac ggagtacacc gcaaccggtc gccccaatcc | 360 |
| ggcgcctaga ccgtgaccca cccgccatct tccgcaagac cgaatcccca acccacccac | 420 |
| catcttccgc cgccccgtc cccgtccccg gccatggatc cgtcgccggc cgtggatccg | 480 |
| tcgccggccg tggatccgtc gccggctgct gaaacccggc ggcgtgcaac cgggaaagga | 540 |
| ggcaaacagc gcggggcaa gcaactagga ttgaagaggc cgccgccgat ttctgtcccg | 600 |
| gccaccccgc ctcctgctgc gacgtcttca tcccctgctg cgccgacggc catcccacca | 660 |
| cgaccaccga atcttcgcc gattttcgtc cccgattcgc cgaatccgtc accggctgcg | 720 |
| ccgacctcct ctcttgcttc ggggacatcg acggcaaggc caccgcaacc acaaggagga | 780 |
| ggatggggac caacatcgac catttcccca aactttgcat cttcttggg aaccaacaa | 840 |
| gacccaaatt catggtacat gtattttctt cttttctgt tactttcaac ctacggtaac | 900 |
| tctaattcat ggatgagact actgccattg tgcagttcaa tgctttttct tcatgttata | 960 |
| tttcgtccag ctgtgagtta tggtttgaag attgctgtgg ttgtttcatt gctgagtatg | 1020 |
| tgaaagatag atggatgaaa gagagaatta tattttagtc tgtaatcttg ctcatccagt | 1080 |
| tgctcatgta tgaccttggt tctagaatgt tgccctgact gtatgcttaa tgttcagaga | 1140 |
| agtgatgcct aaagcagtga gatcagtggg atcagattag ctatcgacat ataatattag | 1200 |
| ctatctcagt tgtgaaagag agatgggtga aaaggcaccc cttggattaa ttctgtagta | 1260 |
| tcaaattctg caccttgtct gtccatatgt tctgcttggt tggtgggtgc agtgcatttg | 1320 |
| taaaaaatag tttgcttctg atccttaata tatgtaacag ggaatgaatt ttcacccatc | 1380 |
| tcagttgtaa aggtactgtc ttgctatgca atatgtgtaa attgacaaac ctgaaaatag | 1440 |
| tctgtttgga atttgcaaaa gcaattcgat agtttggaat ttccaaacct cagtcagcag | 1500 |
| taggcaatcc attttagttc ttgctatgca caaaaacagt acacctgata tgctcatttt | 1560 |
| aatacaactt ttttgtctct gttacagttt ggtcaggggt tatcctccag gagggtttgt | 1620 |
| caatttatt caacaaaatt gtccgccgca gccacaacag caaggtgaaa atttcatttt | 1680 |
| cgttggtcac aatatgggat tcaacccaat atctccacag ccaccaagtg cctacggaac | 1740 |
| accaacaccc caagctacga accaaggcac ttcaacaaac attatgattg atgaagagga | 1800 |
| caacaatgat gacagtaggg cagcaaagaa aagatggact catgaagagg aagagagact | 1860 |
| ggtattcatc ggatactttt acatttccat atgtctttgt tttgactaat acttgacagg | 1920 |

```
tcattaactg attcttgtag gccagtgctt ggttgaatgc ttctaaagac tcaattcatg   1980
ggaatgataa gaaaggtgat acatttggaa aggaagtcac tgatgaattt aacaagaaag   2040
ggaatggaaa acgtaggagg gaaattaacc aactgaaggt tcactggtca aggttgaagt   2100
cagcgatctc tgagttcaat gactattgga gtacggttac tcaaatgcat acaagcggat   2160
actccgacga catgcttgag aaagaggcac agaggctgta tgcaaacagg tttggaaaac   2220
cttttgcgtt ggtccattgg tggaagatac tcaaagatga gcccaaatgg tgtgctcagt   2280
ttgaatcaga gaaagacaag agcgaaatgg atgctgttcc agaacagcag tcacgtccta   2340
ttggtagaga agcagcaaag tctgagcgca atggaaagcg caagaaagaa aatgttatgg   2400
aaggcattgt cctcctaggg gacaatgtcc agaaaattat aaaggtccac gaagaccgga   2460
gggtggatcg tgaaaaggcc accgaagcac agattcagat atcaaatgca acattgttgg   2520
ccgctaagga gcagaaggaa gcaaagatgt tcgatgtgta caatactcta ttaagtaagg   2580
atacaagcaa catgtctgaa gatcaaatgg ctagccacca gagggcaata cggaaattag   2640
aggagaagct atttgcggat taaggtgagt tttataaact gaccactatt ttctgaaatg   2700
tatgaattct gaaatttata tacaattgtg taaacatgga aaattagata atgtatgcat   2760
gatgcacaac atgtgcgtgc agcactattt aatggcagtt tcacaagtgt gaaaactgac   2820
cactatagta ctattgtggt gtgaaaactg accactacta ttgtggtgtg aatgctactg   2880
tggtgtgaaa actgaccact atagtttcac attcctggat gcagccctcc tctatatata   2940
tagatacagt cctcatctct tcctggcata cacacagccc tcttctctaa ttcctggacg   3000
cagtcctcat ctcttcctgg catagacgca gcccttctct cttcctgttt agttcaacaa   3060
cattgaggtg atctgccttt cttttgaagtt tctatctttt ttcactgctg tgaatgatta   3120
tttctctgct gtgaatgatt atttctccaa tcttcctttg ttcaccttct ctctttctct   3180
gctgtgaaga tgtctggaaa tgaaaatcag attcctgtgt ccttgttgga cgagtttctc   3240
gctgaggatg agatcatgga tgagataatg gatgatgttc tccatgaaat gatggtgtta   3300
ttgcagtcct ccatcggaga tcttgaaaga gaggctgctg accatcgttt gcatccaagg   3360
aagcacatca agaggccacg agaggaagca catcaaaatt tggtgaatga ttatttctct   3420
gaaaatcctc tatatccttc caatattttt cgccgaagat ttcgtatgta caggccgctg   3480
tttttacgta ttgtggacgc attaggccag tggtcagatt actttactca gagggtagat   3540
gccgctggta ggcaagggct tagtccatta caaaagtgta ctgcagcaat tcgccaattg   3600
gctactggta gtggtgctga tgaactagat gagtatttga agattggaga gactactgct   3660
atggatgcta tgaaaaattt tgtgaaagga attagagaag tatttggtga agatatctc   3720 aggcgtccca ctgtagaaga tactgaacga ctactcgagc ttggtgagag acgcggtttt   3780
cctggtatgt tcggtagcat tgactgtatg cattggcaat gggaaaggtg cccaactgcg   3840
tggaagggtc agttcactcg tggtgatcaa aaagtgccaa cgctgattct tgaggcagtg   3900
gcatcacatg atctttggat ttggcatgcg ttctttggag tagcaggttc taacaatgat   3960
atcaatgttt tgagccgatc tactgtgttt atcaatgagc tgaaaggaca agctcctaga   4020
gtgcagtaca tggtaaatgg gaatcaatac aacgaaggtt attttcttgc tgatggaatt   4080 tacccctgaat ggaaggtatt tgctaagtca tatcgactcc ctatcactga aaggagaag   4140 ttgtatgcac aacatcaaga aggggcaaga aaggatatcg agagagcatt tggtgttcta   4200
caacgtcgat tctgcatctt aaaacgacca gcccgtctat atgaccgagg tgtactccgt   4260
gatgttgtcc taggttgcat catacttcac aatatgatag ttgaagatga gaaggaagcg   4320
```

```
cgacttattg aagaaaatct agatttaaat gagcctgcta gttcatcaac ggttcaggca    4380
ccagaattct ctcctgacca gcatgttcca ttagaaagaa ttttagaaaa ggatactagt    4440
atgagagatc gtttggctca tcgccgactc aagaatgatt tggtggaaca tatatggaat    4500
aagtttggtg gtggtgcaca ttcatctggt aattatgttt ttattttgca ttattagtta    4560
tctatggtac taagatatgt acaagtttct ctaaattgca ctaaatctgt ggttcatatt    4620
ggatatgtgt aaactatgaa tgtagcctga ctaaaaccat cattcatgct gaactggttt    4680
ttgttttgta tatgcaggat gaaacaagga actaggtttc tgaacgcatt acggactgaa    4740
ggttgagggg cagaatgatc cacccagttg cttctatcag atcactaaag tttcatttca    4800
ctgttttatt ttggacactt gatgcttgtg tgcatccgat gaatgtttaa tttggtcacc    4860
tgatgcttgt gtgcatccga tgaatgttta atttggtcac ctgatgcttg tatgcagtta    4920
tctatcttat ttgttaatgt tgctggtact gaggattttt agaagtgaaa tgcacaagtt    4980
gctgtgtttt tgactgatc cttgtgtgca cttgacgttg tatgtgacaa atgatggttc     5040
ccagttgtgc acctgattca tgattcagtt attcagttta aattgacgtt gtttgtgtgc    5100 acctttgtc agttagccag ttacggctgg aagttgtgta agtttgtgtg acgcctggct     5160
acaggatttt gggtacaaat gatcccagca acttgtatca attaaatgct tgcttagtc     5220 ttggaaacgt caaagtgaaa cccctccact gtggggattg tttcataaaa gatttcattt    5280
gagagaagat ggtataatat tttgggtagc cgtgcaatga cactagccat tgtgactggc    5340
c                                                                    5341

<210> SEQ ID NO 3
<211> LENGTH: 5166
<212> TYPE: DNA
<213> ORGANISM: Oryza sativa

<400> SEQUENCE: 3
ggccagtcac aatgggtgtt tcatttgagt gtcatgcgca tttaatacag tgacaagtca      60
gcaaaagagc aatatttgca tgaaatgggt aggagagaga gtaaactcgt ttcaccatgg     120
tgacacgaga tagcgccgtt tcccaggtcg ctgaaacggg gtgaaacagc attgagagtt     180
catcgtttca cctccgggat cccgtgcgag cgctgctctt cgccatcttc gcgcgcatcg     240
ccggattctt cccgcgcgag tccccatct tcccgcgcag cacctccatg ttcccgcccc      300
caaagcactg gctcgaagct ttttccccca atctcacctg caaccctagc gccagactca     360
gtccccatcg ccccgtccgt cccataccct agcgcaagaa ccacgagcgg agattgcgga     420
gctggatcca caagtaggtg gtgaatcctg tccatctgcc gccgtccgcc gtccagcagc     480
catggatcca caaggaggtg gtggatcccg tctgagcgcc gccggcagag gagggaataa     540
gcgtgggggc aagcagctgg gcctgaagag gtcgtcggcg cctgctccat caccggcaac     600
agctcagcca ccgctgcctg caagttcccc tcctgaagct ccatcgccgg caacagttca     660
gccgcctact ccatcgtcaa gtcctgctgt tgctgccccc agttcatccc ctgctgtacc     720
gatgtcaacc atgccccat ggccaccgca aggagcagga tggggctctg taccccccaa      780
ttttgctttt ctgcaaggaa accaacaagg cccaagttca tggtattttc tccttgtcac     840
agattattca ctgtacacta tgatacatga tatgactctc ttcttcatgc attagtaatt     900
agttcctgtt tatgctcaat gaaatttgtt agaatcagta tgtcagtaca ttggtaattt     960
gatatatgcc tgagtaatga atagaaaaaa tgtagtattc agtatggatt gcagtaatac    1020
tttgttagtg aaaattcagt attcagtatg cagtatggat tgcggcttgt ataacagaaa    1080
```

```
ttgaaagcaa aagattcagt ttgcaatctg gacagtgtac tgtacaacat gtaattcaca    1140
tacgtaaagc ttgttaaata tctccttgtc agtacattgg taacaaatgc tttgagtgta    1200
aatgccaagg gtatcatcct aacattggta tatattttta gccttctgta tggaatgcag    1260
acatggtctt ctttgcaacc acagcaacag cttgccctac actctgtgct gtcgtcatag    1320
ctaaccaaat aacctgttag tactgatata tatggtcttc tttgcaacca cagcaacagc    1380
ttgccctaca tggtcttctg tatgcttgac taaacttgtt acttgacata tatgcttgac    1440
tgaacttgtt gcttgactga attattcctt acacatactg tagtacttgc ttgactgaac    1500
tatgtcagga tcttattaaa aaaaatctat gtcagcactg ctactatgtc aggatcatca    1560
gtatgatgct taagtaacct gttagtatgt cagtacttac tatgtcagga tcatcttctg    1620
gaacttacta tgtttgattt tcttatgctg ccatcggttt caattggatt tgcttcttat    1680
gttttcaggt tgtatcctac agaaggcttc gtaaattttc tccaacagaa ctgtctgccg    1740
cagccacaag aaggtgaaaa ttttcacctt gttggtcaga ctaccaacac aatgtctact    1800
ccaccaccaa caccccaagc tgcagctaac aatacagtcc aaattgatat tcatgaagat    1860
gcaatcaatg atgcaagtgc taaaagagaa gtttgagata ttggactcat gatgaggaa     1920 gagagattgg ctagtgcttg gttgaatgct tctaaagatc ccattcatgg gaatgaaaag    1980
aaaggtgata cgttttggaa agaggttact gatgagttca acagaaaagg gaatgggaag    2040
cgtacaaggg aaataaatca attgaaggtt cattggtcac gcctcaaatc atcgattgga    2100
gaattcaatg attactggac taaggtaact caaatgaata caagcggata tgacgatgac    2160
atgctggaga aggaggcaca acagatgtat gcaaatacat ttggaaagcc ttttgcactt    2220
gtgcattggt ggaagatact gagaaaagag cccaagtggt gtgcaatgat tgagaaggac    2280
aaaaacaagg ctgaagtggt tgatattcca gatgaacaaa agcgtcccat ggtagagaa     2340 gcagcacaag ccgagcgcaa tggaaaacgc aagaaggaca gtatgtcaga aggaattgtc    2400
atcctagggg acaatattga aaaaattatc aaagtgacgc aagatcggaa gctggagcgt    2460
gagaaggtca ctgaagcaca gattcacatt tcaaacgtaa atttgaaggc agcagaacag    2520
caaaaagaag caaagatgtt tgaggtatac aattccctgc tcactcaaga tacaagtaac    2580
atgtctgaag aacagaaggc tcgccgagac aaggcattac aaaagctgga ggaaaagtta    2640
tttgctgact aaggttagat atctaatcta atctgagctg cactattatt tataataatt    2700
aaagaatgct gcaatattta gttatattgt ctgtatatct gtgctgcact atgcagtcag    2760
ctgcatatca cgaatttgtc aaatctgagc tgcatatctg tgaatggtgc aatatttagt    2820
tatattaatt acccagtgtg aatgatgtat tgctgtcagt ttcacatata gtatgaatgc    2880
tgcactatgc agtcagtttc acatgcagtg tgaatgctgc actaggcagt cagtttcaca    2940
tgcagtgggc gcctatttat gcagagttta gccatctctc tactcctctc agaaactcat    3000
tccctctttt ctcatacgaa gacctcctcc cttttatctt tactgtttct ctcttcttca    3060
aagatgtctg agcaaaatac tgatggaagt caagttccag tgaacttgtt ggatgagttc    3120
ctggctgagg atgagatcat agatgatctt ctcactgaag ccacggtggt agtacagtcc    3180
actatagaag gtcttcaaaa cgaggcttct gaccatcgac atcatccgag gaagcacatc    3240
aagaggccac gagaggaagc acatcagcaa ctagtgaatg attactttc agaaaatcct     3300 ctttacccct tccaaaatttt tcgtcgaaga tttcgtatgt ctaggccact ttttcttcgc    3360
atcgttgagg cattaggcca gtggtcagtg tatttcacac aaagggtgga tgctgttaat    3420
cggaaaggac tcagtccact gcaaaagtgt actgcagcta ttcgccagtt ggctactggt    3480
```

-continued

```
agtggcgcag atgaactaga tgaatatctg aagataggag agactacagc aatggaggca      3540
atgaagaatt ttgtcaaagg tcttcaagat gtgtttggtg agaggtatct taggcgcccc      3600
accatggaag ataccgaacg gcttctccaa cttggtgaga acgtggtttt tcctggaatg      3660
ttcggcagca ttgactgcat gcactggcat tgggaaagat gcccagtagc atggaagggt      3720
cagttcactc gtggagatca gaaagtgcca accctgattc ttgaggctgt ggcatcgcat      3780
gatctttgga tttggcatgc attttttgga gcagcgggtt ccaacaatga tatcaatgta      3840
ttgaaccaat ctactgtatt tatcaaggag ctcaaaggac aagctcctag agtccagtac      3900
atggtaaatg ggaatcaata caatactggg tattttcttg ctgatggaat ctaccctgaa      3960
tgggcagtgt ttgttaagtc aatacgactc ccaaacactg aaaaggagaa attgtatgca      4020
gatatgcaag aaggggcaag aaaagatatc gagagagcct ttggtgtatt gcagcgaaga      4080
ttttgcatct taaaacgacc agctcgtcta tatgatcgag gtgtactgcg agatgttgtt      4140
ctagcttgca tcatacttca caatatgata gttgaagatg agaaggaaac cagaattatt      4200
gaagaagatt tagatctaaa tgtgcctcct agttcatcaa ccgttcagga acctgagttc      4260
tctcctgaac agaacacacc atttgataga gttttagaaa aagatatttc tatccgagat      4320
cgagcggctc ataaccgact taagaaagat ttggtggaac acatttggaa taagtttggt      4380
ggtgctgcac atagaactgg aaattgagaa tcagtaaatg taattatttt attttctttg      4440
taatttatat atctatggtc cacttgtaaa tttctgaatg ctcatcgcca tatttttaa      4500 tctctgcagg ttccaatcta tttacaggtt ccctaaaaaa aaatctattt gcaggttcca      4560
gtctgttgtc ttcacaatgt aagttctgag aatcaaatca ctatgttttt ctctttttg      4620 gtagctacag ggtgttagaa catgtgttat tttctttact atgcaattgt gatcctccaa      4680
tatttatcta ctgcatgtgt aaacctgttt gtcatgtctg aactactttc atttgtacag      4740
ggtgaaagaa tcaatgaaat ctatgggtgc atcgtcaatt tgcctccagt tacctgcttg      4800
tcatcgtcat ttgtagctta gttctgtcat atttcacctc gagttaacat ctattcagtt      4860
atctaaactt tgctatgtag tgaacttggt tgaatggtca tttaaattta tcaagtgaac      4920
aatcgtacct atctgtgctg aatgcatgta ttttgttttg tgttcaagtg gctacacacg      4980
tttgtgttac atacgatccc actatgtggc tggaattaaa tgccttgaat ttgcattgga      5040
aacgctagag tgaaacacag cattgagaag gtctgtttca ttgtacgttt caacttgttt      5100
catcttcgtt tcagctgatg tggcgtctgg gaaacagtgt aatgaaacac tgcattgtga      5160
atggcc                                                                5166
```

<210> SEQ ID NO 4
<211> LENGTH: 455
<212> TYPE: PRT
<213> ORGANISM: Oryza sativa

<400> SEQUENCE: 4

```
Met Ser Gly Asn Glu Asn Gln Ile Pro Val Ser Leu Leu Asp Glu Phe
 1               5                  10                  15

Leu Ala Glu Asp Glu Ile Met Asp Glu Ile Met Asp Asp Val Leu His
                20                  25                  30

Glu Met Met Val Leu Leu Gln Ser Ser Ile Gly Asp Leu Glu Arg Glu
            35                  40                  45

Ala Ala Asp His Arg Leu His Pro Arg Lys His Ile Lys Arg Pro Arg
        50                  55                  60
```

-continued

```
Glu Glu Ala His Gln Asn Leu Val Asn Asp Tyr Phe Ser Glu Asn Pro
 65                  70                  75                  80

Leu Tyr Pro Ser Asn Ile Phe Arg Arg Phe Arg Met Tyr Arg Pro
                 85                  90                  95

Leu Phe Leu Arg Ile Val Asp Ala Leu Gly Gln Trp Ser Asp Tyr Phe
            100                 105                 110

Thr Gln Arg Val Asp Ala Ala Gly Arg Gln Gly Leu Ser Pro Leu Gln
            115                 120                 125

Lys Cys Thr Ala Ala Ile Arg Gln Leu Ala Thr Gly Ser Gly Ala Asp
130                 135                 140

Glu Leu Asp Glu Tyr Leu Lys Ile Gly Glu Thr Thr Ala Met Asp Ala
145                 150                 155                 160

Met Lys Asn Phe Val Lys Gly Ile Arg Glu Val Phe Gly Glu Arg Tyr
                165                 170                 175

Leu Arg Arg Pro Thr Val Glu Asp Thr Glu Arg Leu Leu Glu Leu Gly
            180                 185                 190

Glu Arg Arg Gly Phe Pro Gly Met Phe Gly Ser Ile Asp Cys Met His
            195                 200                 205

Trp Gln Trp Glu Arg Cys Pro Thr Ala Trp Lys Gly Gln Phe Thr Arg
            210                 215                 220

Gly Asp Gln Lys Val Pro Thr Leu Ile Leu Glu Ala Val Ala Ser His
225                 230                 235                 240

Asp Leu Trp Ile Trp His Ala Phe Phe Gly Val Ala Gly Ser Asn Asn
                245                 250                 255

Asp Ile Asn Val Leu Ser Arg Ser Thr Val Phe Ile Asn Glu Leu Lys
            260                 265                 270

Gly Gln Ala Pro Arg Val Gln Tyr Met Val Asn Gly Asn Gln Tyr Asn
            275                 280                 285

Glu Gly Tyr Phe Leu Ala Asp Gly Ile Tyr Pro Glu Trp Lys Val Phe
            290                 295                 300

Ala Lys Ser Tyr Arg Leu Pro Ile Thr Glu Lys Glu Lys Leu Tyr Ala
305                 310                 315                 320

Gln His Gln Glu Gly Ala Arg Lys Asp Ile Glu Arg Ala Phe Gly Val
                325                 330                 335

Leu Gln Arg Arg Phe Cys Ile Leu Lys Arg Pro Ala Arg Leu Tyr Asp
            340                 345                 350

Arg Gly Val Leu Arg Asp Val Val Leu Gly Cys Ile Ile Leu His Asn
            355                 360                 365

Met Ile Val Glu Asp Glu Lys Glu Ala Arg Leu Ile Glu Glu Asn Leu
370                 375                 380

Asp Leu Asn Glu Pro Ala Ser Ser Thr Val Gln Ala Pro Glu Phe
385                 390                 395                 400

Ser Pro Asp Gln His Val Pro Leu Glu Arg Ile Leu Glu Lys Asp Thr
                405                 410                 415

Ser Met Arg Asp Arg Leu Ala His Arg Arg Leu Lys Asn Asp Leu Val
            420                 425                 430

Glu His Ile Trp Asn Lys Phe Gly Gly Ala His Ser Ser Gly Asn
            435                 440                 445

Tyr Val Phe Ile Leu His Tyr
450                 455
```

<210> SEQ ID NO 5
<211> LENGTH: 482
<212> TYPE: PRT
<213> ORGANISM: Oryza sativa

<400> SEQUENCE: 5

```
Met Gln Ser Leu Ala Ile Ser Leu Leu Ser Glu Thr His Ser Leu
1               5                   10                  15

Phe Ser His Thr Lys Thr Ser Leu Ser Leu Phe Leu Ser
            20                  25                  30

Ser Ser Lys Met Ser Glu Gln Asn Thr Asp Gly Ser Gln Val Pro Val
            35                  40                  45

Asn Leu Leu Asp Glu Phe Leu Ala Glu Asp Glu Ile Ile Asp Asp Leu
    50                  55                  60

Leu Thr Glu Ala Thr Val Val Gln Ser Thr Ile Glu Gly Leu Gln
65                  70                  75                  80

Asn Glu Ala Ser Asp His Arg His Pro Arg Lys His Ile Lys Arg
                85                  90                  95

Pro Arg Glu Glu Ala His Gln Gln Leu Val Asn Asp Tyr Phe Ser Glu
                100                 105                 110

Asn Pro Leu Tyr Pro Ser Lys Ile Phe Arg Arg Phe Arg Met Ser
            115                 120                 125

Arg Pro Leu Phe Leu Arg Ile Val Glu Ala Leu Gly Gln Trp Ser Val
    130                 135                 140

Tyr Phe Thr Gln Arg Val Asp Ala Val Asn Arg Lys Gly Leu Ser Pro
145                 150                 155                 160

Leu Gln Lys Cys Thr Ala Ala Ile Arg Gln Leu Ala Thr Gly Ser Gly
                165                 170                 175

Ala Asp Glu Leu Asp Glu Tyr Leu Lys Ile Gly Glu Thr Thr Ala Met
                180                 185                 190

Glu Ala Met Lys Asn Phe Val Lys Gly Leu Gln Asp Val Phe Gly Glu
                195                 200                 205

Arg Tyr Leu Arg Arg Pro Thr Met Glu Asp Thr Glu Arg Leu Leu Gln
    210                 215                 220

Leu Gly Glu Lys Arg Gly Phe Pro Gly Met Phe Gly Ser Ile Asp Cys
225                 230                 235                 240

Met His Trp His Trp Glu Arg Cys Pro Val Ala Trp Lys Gly Gln Phe
                245                 250                 255

Thr Arg Gly Asp Gln Lys Val Pro Thr Leu Ile Leu Glu Ala Val Ala
            260                 265                 270

Ser His Asp Leu Trp Ile Trp His Ala Phe Phe Gly Ala Ala Gly Ser
        275                 280                 285

Asn Asn Asp Ile Asn Val Leu Asn Gln Ser Thr Val Phe Ile Lys Glu
    290                 295                 300

Leu Lys Gly Gln Ala Pro Arg Val Gln Tyr Met Val Asn Gly Asn Gln
305                 310                 315                 320

Tyr Asn Thr Gly Tyr Phe Leu Ala Asp Gly Ile Tyr Pro Glu Trp Ala
                325                 330                 335

Val Phe Val Lys Ser Ile Arg Leu Pro Asn Thr Glu Lys Glu Lys Leu
                340                 345                 350

Tyr Ala Asp Met Gln Glu Gly Ala Arg Lys Asp Ile Glu Arg Ala Phe
            355                 360                 365

Gly Val Leu Gln Arg Arg Phe Cys Ile Leu Lys Arg Pro Ala Arg Leu
    370                 375                 380
```

```
Tyr Asp Arg Gly Val Leu Arg Asp Val Val Leu Ala Cys Ile Ile Leu
385                 390                 395                 400

His Asn Met Ile Val Glu Asp Glu Lys Glu Thr Arg Ile Ile Glu Glu
                405                 410                 415

Asp Leu Asp Leu Asn Val Pro Pro Ser Ser Ser Thr Val Gln Glu Pro
            420                 425                 430

Glu Phe Ser Pro Glu Gln Asn Thr Pro Phe Asp Arg Val Leu Glu Lys
        435                 440                 445

Asp Ile Ser Ile Arg Asp Arg Ala Ala His Asn Arg Leu Lys Lys Asp
    450                 455                 460

Leu Val Glu His Ile Trp Asn Lys Phe Gly Ala Ala His Arg Thr
465                 470                 475                 480

Gly Asn
```

<210> SEQ ID NO 6
<211> LENGTH: 900
<212> TYPE: DNA
<213> ORGANISM: Oryza sativa

<400> SEQUENCE: 6

```
tttcaagtac aatctcaact tagggaaagt tgtgattgag ggaggatgtt agataatgtt    60
agttagtttg ttatagagat agattagttc tgttaccgca tgtactttct tgtatctatc   120
tctatatcca ggattgtctc aggttgttga gattaatcct atcctttgta cacgccacgg   180
tagaggctct ttctgcctat atcaacaaag gtgcggcccc gtaaagggt tcaacgcttc    240
tcattccgtt ttacaatcct ccttcttcct cctggtgttg gaaattcgtt gatcgagttg   300
aaactctcat ccttcatcat gtgctgcaga aactaacgcg tgcacagatg atggatgggt   360
gtggtgtgac atgaaagtgg atcaatgaca cgcggcacat ttaggggagt gtgtcgtgtc   420
ttgacttctt catgcaaaag tataccaacc ctgtataagg ccagtcacaa tggctagtgt   480
cattgcacgg ctacccaaaa tattatacca tcttctctca aatgaaatct tttatgaaac   540
atccccaca gtggagggt tcactttga cgtttccaag actaagcaaa gcatttaatt     600
gatacaagtt gctgggatca tttgtaccca aaatccggcg cggcgcggga gaatgcggag   660
gtcgcacggc ggaggcggac gcaagagatc cggtgaatga aacgaatcgg cctcaacggg   720
ggtttcactc tgttaccgag gacttggaaa cgacgctgac gagtttcacc aggatgaaac   780
tctttccttc tctctcatcc ccatttcatg caaataatca ttttttattc agtcttaccc   840
ctattaaatg tgcatgacac accagtgaaa ccccccattgt gactggccta agcatctttg   900
```

<210> SEQ ID NO 7
<211> LENGTH: 18
<212> TYPE: DNA
<213> ORGANISM: Artificial Sequence
<220> FEATURE:
<223> OTHER INFORMATION: PCR primer

<400> SEQUENCE: 7

```
ttaggccagt cacaatgg                                                  18
```

<210> SEQ ID NO 8
<211> LENGTH: 24
<212> TYPE: DNA
<213> ORGANISM: Artificial Sequence
<220> FEATURE:
<223> OTHER INFORMATION: PCR primer -continued

```
<400> SEQUENCE: 8
gtgcgtggtt ggtctcggct ttat                                  24

<210> SEQ ID NO 9
<211> LENGTH: 24
<212> TYPE: DNA
<213> ORGANISM: Artificial Sequence
<220> FEATURE:
<223> OTHER INFORMATION: PCR primer

<400> SEQUENCE: 9
cctccttctt cctcctggtg ttgg                                  24

<210> SEQ ID NO 10
<211> LENGTH: 28
<212> TYPE: DNA
<213> ORGANISM: Artificial Sequence
<220> FEATURE:
<223> OTHER INFORMATION: PCR primer

<400> SEQUENCE: 10
gtaagactga ataaaaaatg attatttg                              28

<210> SEQ ID NO 11
<211> LENGTH: 26
<212> TYPE: DNA
<213> ORGANISM: Artificial Sequence
<220> FEATURE:
<223> OTHER INFORMATION: PCR primer

<400> SEQUENCE: 11
catcttctct caaatgaaat cttttta                               26

<210> SEQ ID NO 12
<211> LENGTH: 23
<212> TYPE: DNA
<213> ORGANISM: Artificial Sequence
<220> FEATURE:
<223> OTHER INFORMATION: PCR primer

<400> SEQUENCE: 12
atgtagtttg tcggtaagtt tga                                   23

<210> SEQ ID NO 13
<211> LENGTH: 23
<212> TYPE: DNA
<213> ORGANISM: Artificial Sequence
<220> FEATURE:
<223> OTHER INFORMATION: PCR primer

<400> SEQUENCE: 13
atgtgttgtg attgatggga taa                                   23

<210> SEQ ID NO 14
<211> LENGTH: 30
<212> TYPE: DNA
<213> ORGANISM: Artificial Sequence
<220> FEATURE:
<223> OTHER INFORMATION: PCR primer

<400> SEQUENCE: 14
gggtgagtga agtgagtgag tgagcagcat                            30
```

```
<210> SEQ ID NO 15
<211> LENGTH: 30
<212> TYPE: DNA
<213> ORGANISM: Artificial Sequence
<220> FEATURE:
<223> OTHER INFORMATION: PCR primer

<400> SEQUENCE: 15 agttaggga ggagagttgg gcataggaat                                    30

<210> SEQ ID NO 16
<211> LENGTH: 23
<212> TYPE: DNA
<213> ORGANISM: Artificial Sequence
<220> FEATURE:
<223> OTHER INFORMATION: PCR primer

<400> SEQUENCE: 16
gcctcctgct gcgacgtctt cat                                          23

<210> SEQ ID NO 17
<211> LENGTH: 30
<212> TYPE: DNA
<213> ORGANISM: Artificial Sequence
<220> FEATURE:
<223> OTHER INFORMATION: PCR primer

<400> SEQUENCE: 17
caactggatg agcaagatta cagactaaaa                                   30

<210> SEQ ID NO 18
<211> LENGTH: 24
<212> TYPE: DNA
<213> ORGANISM: Artificial Sequence
<220> FEATURE:
<223> OTHER INFORMATION: PCR primer

<400> SEQUENCE: 18
cagtacgcca ccaatcacca tcat                                         24

<210> SEQ ID NO 19
<211> LENGTH: 24
<212> TYPE: DNA
<213> ORGANISM: Artificial Sequence
<220> FEATURE:
<223> OTHER INFORMATION: PCR primer

<400> SEQUENCE: 19
ctcatctcga acgcaaccta aata                                         24

<210> SEQ ID NO 20
<211> LENGTH: 25
<212> TYPE: DNA
<213> ORGANISM: Artificial Sequence
<220> FEATURE:
<223> OTHER INFORMATION: PCR primer

<400> SEQUENCE: 20
tgtgatgaac agaacaccac cgaga                                        25

<210> SEQ ID NO 21
<211> LENGTH: 25
<212> TYPE: DNA
<213> ORGANISM: Artificial Sequence
<220> FEATURE:
<223> OTHER INFORMATION: PCR primer
```

<400> SEQUENCE: 21
cccaaagata cagagcacct acaca                                          25

<210> SEQ ID NO 22
<211> LENGTH: 21
<212> TYPE: DNA
<213> ORGANISM: Artificial Sequence
<220> FEATURE:
<223> OTHER INFORMATION: PCR primer

<400> SEQUENCE: 22
tgatccagat acaacctcca t                                              21

<210> SEQ ID NO 23
<211> LENGTH: 21
<212> TYPE: DNA
<213> ORGANISM: Artificial Sequence
<220> FEATURE:
<223> OTHER INFORMATION: PCR primer

<400> SEQUENCE: 23
gaaaagaaaa acaaacaaga a                                              21

<210> SEQ ID NO 24
<211> LENGTH: 30
<212> TYPE: DNA
<213> ORGANISM: Artificial Sequence
<220> FEATURE:
<223> OTHER INFORMATION: PCR primer

<400> SEQUENCE: 24
gggtgagtga agtgagtgag tgagcagcat                                     30

<210> SEQ ID NO 25
<211> LENGTH: 30
<212> TYPE: DNA
<213> ORGANISM: Artificial Sequence
<220> FEATURE:
<223> OTHER INFORMATION: PCR primer

<400> SEQUENCE: 25
agttagggga ggagagttgg gcataggaat                                     30

<210> SEQ ID NO 26
<211> LENGTH: 21
<212> TYPE: DNA
<213> ORGANISM: Artificial Sequence
<220> FEATURE:
<223> OTHER INFORMATION: PCR primer

<400> SEQUENCE: 26
cctcacaacc aatccctacc a                                              21

<210> SEQ ID NO 27
<211> LENGTH: 21
<212> TYPE: DNA
<213> ORGANISM: Artificial Sequence
<220> FEATURE:
<223> OTHER INFORMATION: PCR primer

<400> SEQUENCE: 27
agccaccaca ataaccaaag t                                              21